(12) United States Patent
Jain et al.

(10) Patent No.: US 12,201,720 B2
(45) Date of Patent: *Jan. 21, 2025

(54) PHARMACEUTICAL COMPOSITION COMPRISING GHB GASTRO-RETENTIVE RAFT FORMING SYSTEMS HAVING TRIGGER PULSE DRUG RELEASE

(71) Applicant: Tris Pharma, Inc., Monmouth Junction, NJ (US)

(72) Inventors: Paras Rameshlal Jain, Dayton, NJ (US); Sachin Vasant Chaudhari, Dayton, NJ (US)

(73) Assignee: TRIS PHARMA INC, Monmouth Junction, NJ (US)

( * ) Notice: Subject to any disclaimer, the term of this patent is extended or adjusted under 35 U.S.C. 154(b) by 39 days.

This patent is subject to a terminal disclaimer.

(21) Appl. No.: 17/725,677

(22) Filed: Apr. 21, 2022

(65) Prior Publication Data

US 2022/0241190 A1 Aug. 4, 2022

Related U.S. Application Data

(63) Continuation of application No. 16/955,392, filed as application No. PCT/US2018/066299 on Dec. 18, 2018, now Pat. No. 11,337,920.
(Continued)

(51) Int. Cl.
*A61K 9/00* (2006.01)
*A61K 9/10* (2006.01)
(Continued)

(52) U.S. Cl.
CPC .......... *A61K 9/0065* (2013.01); *A61K 9/1611* (2013.01); *A61K 9/1623* (2013.01);
(Continued)

(58) Field of Classification Search
CPC ................ A61K 9/0065; A61K 9/1611; A61K 9/1623; A61K 9/1635; A61K 9/1652;
(Continued)

(56) References Cited

U.S. PATENT DOCUMENTS

| 3,138,525 A | 6/1964 | Koff |
| 3,499,960 A | 3/1970 | Stauffer et al. |

(Continued)

FOREIGN PATENT DOCUMENTS

| JP | S62195323 | 8/1987 |
| WO | WO 2007/001300 A1 | 1/2007 |

(Continued)

OTHER PUBLICATIONS

Pharmacentral [online] retrieved on Oct. 19, 2023 from: https://pharmacentral.com/product/ammonio-methcrylate-copolymer-pharmaceutical-coating/#:~:text=Ammonio%20Methcrylate%20Copolymer%20Type%20A,pH%2Ddependent%20drug%20release; 6 pages. (Year: 2023).*

(Continued)

*Primary Examiner* — Ernst V Arnold
(74) *Attorney, Agent, or Firm* — Howson & Howson LLP; Cathy A. Kodroff

(57) ABSTRACT

An orally administrable drug powder composition which forms a gastro-retentive RAFT having at least two trigger pulses is provide. The composition contains, at a minimum, (a) at least one GHB drug in a first pulse release which releases in less than about 3 hours; (b) at least one GHB drug in a delayed trigger release form; (c) at least one non-toxic gas generating agent; and (d) a RAFT system, wherein following oral ingestion, the composition provides a self-assembling gastro-retentive RAFT having entrapped therein, the at least one drug of (a) and (b) and the gas generated in situ by the non-toxic gas generating agent, thereby providing (Continued)

Figure 1A:
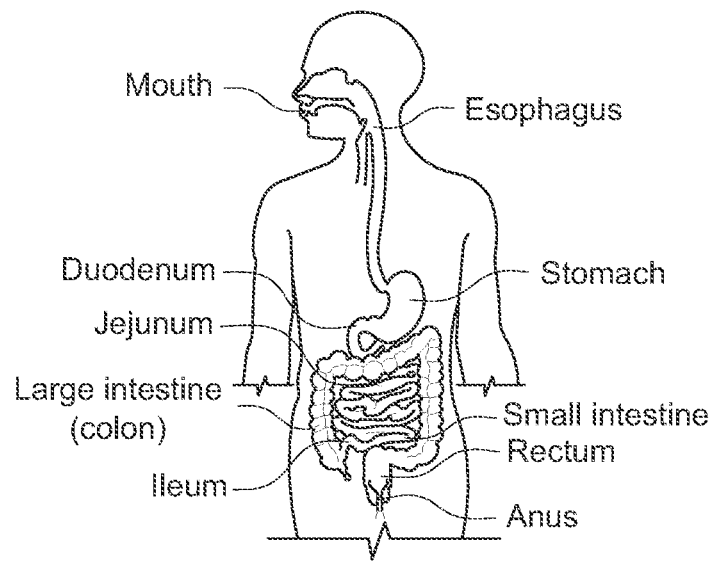

a floating gastro-retentive RAFT having a dual pulse system wherein at least the second pulse is a trigger pulse and which retains the at least one GHB drug in the stomach for at least about 3 hours.

12 Claims, 3 Drawing Sheets

Related U.S. Application Data

(60) Provisional application No. 62/607,159, filed on Dec. 18, 2017.

(51) Int. Cl.
  *A61K 9/16* (2006.01)
  *A61K 9/50* (2006.01)
  *A61K 31/19* (2006.01)
  *A61K 47/50* (2017.01)

(52) U.S. Cl.
  CPC .......... *A61K 9/1635* (2013.01); *A61K 9/1652* (2013.01); *A61K 9/5078* (2013.01)

(58) Field of Classification Search
  CPC ...... A61K 9/5078; A61K 9/0095; A61K 9/10; A61K 9/1617; A61K 9/1664; A61K 9/5146; A61K 31/19; A61K 47/585; A61K 45/06
  See application file for complete search history.

(56) References Cited

U.S. PATENT DOCUMENTS

| | | | |
|---|---|---|---|
| 3,901,232 A | 8/1975 | Michaels et al. | |
| 4,221,778 A | 9/1980 | Raghunathan | |
| 4,352,891 A | 10/1982 | Quinlan | |
| 4,393,236 A | 7/1983 | Klosa | |
| 4,575,539 A | 3/1986 | DeCrosta et al. | |
| 4,844,905 A | 7/1989 | Ichikawa et al. | |
| 4,847,077 A | 7/1989 | Raghunathan | |
| 4,996,047 A | 2/1991 | Kelleher et al. | |
| 5,368,852 A | 11/1994 | Umemoto et al. | |
| 5,604,927 A | 2/1997 | Moore | |
| 5,780,057 A | 6/1998 | Conte et al. | |
| 5,808,107 A | 9/1998 | Hollingsworth | |
| 5,908,631 A | 6/1999 | Arnaud et al. | |
| 5,972,389 A | 10/1999 | Shell et al. | |
| 5,980,882 A | 11/1999 | Eichman | |
| 5,990,162 A | 11/1999 | Scharf | |
| 6,022,562 A | 2/2000 | Autant et al. | |
| 6,120,803 A | 9/2000 | Wong et al. | |
| 6,187,323 B1 | 2/2001 | Aiache et al. | |
| 6,340,475 B2 | 1/2002 | Shell et al. | |
| 6,488,962 B1 | 12/2002 | Berner et al. | |
| 6,713,639 B1 | 3/2004 | Gurjar et al. | |
| 7,294,347 B2 | 11/2007 | Menjoge et al. | |
| 7,405,238 B2 | 7/2008 | Markey et al. | |
| 7,413,751 B2 | 8/2008 | Devane et al. | |
| 7,682,629 B1 | 3/2010 | Besse | |
| 7,906,145 B2 | 3/2011 | Castan et al. | |
| 7,910,133 B2 | 3/2011 | Castan et al. | |
| 7,976,870 B2 | 7/2011 | Berner et al. | |
| 8,062,667 B2 | 11/2011 | Mehta et al. | |
| 8,193,211 B2 | 6/2012 | Liang et al. | |
| 8,202,542 B1 | 6/2012 | Mehta et al. | |
| 8,263,650 B2 | 9/2012 | Cook et al. | |
| 8,277,843 B2 | 10/2012 | Singh et al. | |
| 8,287,848 B2 | 10/2012 | Mehta et al. | |
| 8,313,770 B2 | 11/2012 | Pathak et al. | |
| 8,318,210 B2 | 11/2012 | Tengler et al. | |
| 8,324,275 B2 | 12/2012 | Cook et al. | |
| 8,470,375 B1 | 6/2013 | McMahen et al. | |
| 8,512,759 B1 | 8/2013 | McMahen et al. | |
| 8,586,083 B2 | 11/2013 | Mohammad | |
| 8,591,922 B1 | 11/2013 | Allphin et al. | |
| 8,592,481 B2 | 11/2013 | Berner et al. | |
| 8,668,929 B2 | 3/2014 | Han et al. | |
| 8,747,902 B2 | 6/2014 | Mehta et al. | |
| 8,778,396 B2 | 6/2014 | Pillay et al. | |
| 8,790,700 B2 | 7/2014 | Mehta et al. | |
| 8,802,157 B2 | 8/2014 | Berner et al. | |
| 8,859,619 B2 | 10/2014 | Cook et al. | |
| 8,901,173 B2 | 12/2014 | Allphin et al. | |
| 9,000,046 B2 | 4/2015 | Berner et al. | |
| 9,132,107 B2 | 9/2015 | Allphin et al. | |
| 9,161,911 B2 | 10/2015 | Hou | |
| 9,301,934 B2 | 4/2016 | Berner et al. | |
| 9,439,851 B2 | 9/2016 | Dharmadhkari et al. | |
| 9,566,258 B2 | 2/2017 | Hou | |
| 9,555,017 B2 | 12/2017 | Allphin et al. | |
| 10,092,511 B2 | 10/2018 | Castan et al. | |
| 10,398,662 B1 | 9/2019 | Allphin et al. | |
| 11,337,919 B2 | 5/2022 | Jain et al. | |
| 11,337,920 B2 * | 5/2022 | Jain ..................... | A61K 9/1611 |
| 11,666,546 B2 | 6/2023 | Jain et al. | |
| 2002/0037941 A1 | 3/2002 | Lau et al. | |
| 2003/0099711 A1 | 5/2003 | Meadows et al. | |
| 2004/0092455 A1 | 5/2004 | Mamelak et al. | |
| 2004/0219186 A1 | 11/2004 | Ayres | |
| 2005/0136114 A1 | 6/2005 | Kulkarni et al. | |
| 2006/0062844 A1 | 3/2006 | Chenevier et al. | |
| 2006/0210630 A1 | 9/2006 | Liang et al. | |
| 2007/0036843 A1 | 2/2007 | Hirsh et al. | |
| 2007/0148239 A1 | 6/2007 | Hall et al. | |
| 2007/0215511 A1 | 9/2007 | Mehta et al. | |
| 2009/0275530 A1 | 11/2009 | Tester et al. | |
| 2012/0076865 A1 | 3/2012 | Allphin et al. | |
| 2013/0142846 A1 | 6/2013 | Lee et al. | |
| 2016/0128981 A1 | 5/2016 | Chen et al. | |
| 2016/0228379 A1 | 8/2016 | Kumar et al. | |
| 2016/0317388 A1 | 11/2016 | Bhargava et al. | |
| 2021/0015744 A1 | 1/2021 | Jain et al. | |
| 2022/0241189 A1 | 8/2022 | Jain et al. | |
| 2022/0241190 A1 | 8/2022 | Jain et al. | |
| 2023/0248676 A1 | 8/2023 | Jain et al. | |

FOREIGN PATENT DOCUMENTS

| | | |
|---|---|---|
| WO | WO 2007/010400 | 1/2007 |
| WO | WO 2007/109104 A3 | 9/2007 |
| WO | WO 2011/018582 | 2/2011 |
| WO | WO 2011/119839 A1 | 9/2011 |
| WO | WO 2012/107652 A1 | 8/2012 |
| WO | WO 2013/188413 A1 | 12/2013 |
| WO | WO2015/166473 A1 | 11/2015 |
| WO | WO 2015/186108 A1 | 12/2015 |
| WO | WO 2016/066256 A1 | 5/2016 |
| WO | WO 2016/087952 A1 | 6/2016 |
| WO | WO 2019/126215 A1 | 6/2019 |
| WO | WO 2019/126216 A1 | 6/2019 |
| WO | WO 2019/126218 A1 | 6/2019 |

OTHER PUBLICATIONS

Banerjee S et al., Investigation on crosslinking density for development of novel interpenetrating polymer network (IPN) based formulation, Journal of Scientific and Industrial Research, 2010, 69(10):777-784.

Bhardwaj V et al., Interpenetrating Polymer Network (IPN): Novel approach in Drug delivery, Int. J. Drug Dev. Res., 4(3), Jul.-Sep. 2012.

Bhardwaj L et al., A Short Review on Gastro Retentive Formulations for Stomach Specific Drug Delivery: Special Emphasis on Floating In situ Gel Systems, African J of Basic & Applied Sciences, 2011, 3(6):300-312.

Hanninen K et al., Mechanistic evaluation of factors affecting compound loading into ion-exchange fibers, Eur. J. Pharm. Sci., 2007, 31(5): 306-317.

Koul V et al., Interpenetrating polymer network (IPN) nanogels

(56) References Cited

OTHER PUBLICATIONS based on gelatin and poly(acrylic acid) by inverse mini-emulsion technique: synthesis and characterization, Colloids Surf. B. Biointerfaces, 2011, 83(2):2014-213.

Koshmala JD et al., Preparation of interpenetrating networks of gelatin and dextran as degradable biomaterials, Biomaterials, 2000, 21(20):2019-2023.

Landfester K et al., Synthesis of colloidal particles in miniemulsions, Annual Review of Materials Research, 2006, 36:231-279.

Lohani A et al., Interpenetrating Polymer Networks as Innovative Drug Delivery Systems, Journal of Drug Delivery, 2014, 2014:1-11.

Lu J et al., One-step synthesis of interpenetrating network hydrogels: Environment sensitivities and drug delivery properties, Saudi J. Biol. Sci. 2016, 2016(3):S22-S31.

Nirmal HB et al., In-Situ gel: New trends in Controlled and Sustained Drug Delivery System, Int. J. of Pharm Tech Research, 2010, 2(2):1398-1408.

Guar, P. et al. Ion Exchange Resins in Gastroretentive Drug Delivery: Characteristics, Selection, Formulation and Applications *International Journal of Pharmacology and Pharmaceutical Sciences,* Dec. 2014, 1:304-312.

Yashwantrao PA et al., A Raft Forming System: An Novel Approach for Gastroretention, Int. J. Pure App. Biosci., 2015, 3(4):178-192.

Shailaja P et al., A Review on Gastroretentive Drug Delivery System, International Journal of Research and Development in Pharmacy and Life Sciences, 2016, 5(4):2178-2187.

Sharma AR and Khan A, Gastroretentive Drug Delivery System: An Approach to Enhance Gastric Retention for Prolonged Drug Release, International Journal of Pharmaceutical Sciences and Research, 2014, 5(4):1095-1106.

Subrahmanyam PJ, Design and development of guar gum and borax crosslinked guar gum matrix tablets of theophylline for colon specific drug, Journal of Chemical and Pharmaceutical Research, 2012, 4(2):1052-1060.

Rajesh AM et al., Taste masking of ciprofloxacin by ion-exchange resin and sustain release at gastric-intestinal through interpenetrating polymer network, Asian Journal of Pharmaceutical Sciences, 2015, 10(2015):331-340.

Rajesh AM et al., Taste masking of ofloxacin and formation of interpenetrating polymer network beads for sustained release, Journal of Pharmaceutical Analysis, 2017, 7(2017):244-251.

El Nabarawi MA et al., Formulation, release characteristics, and bioavailability study of gastroretentive floating matrix tablet and floating raft system of Mebeverine HCI, Drug Design, Development and Therapy, 2017, 11:1081-1093.

Shah SH et al., Stomach Specific Floating Drug Delivery System: A Review, International Journal of PharmTech Research, 2009, 1(3):623-633.

Gupta KC and Ravi Kumar MNV, Semi-interpenetrating polymer network beads of crosslinked chitosan-glycine for controlled release of chlorophenramine maleate, Journal of Applied Polymer Science, 2000, 76(5):672-683.

Thakral, S. et al. Eudragit®: a technology evaluation *Expert Opinion on Drug Delivery,* Oct. 26, 2012, 10(1):131-149.

Qadri MF et al, Biomedical Applications of Interpenetrating Polymer Network System, Open Pharmaceutical Sciences Journal, 2015, 2:21-30.

Sperling LH and Hu R, Interpenetrating Polymer Networks, Polymer Blends Handbook, 2003, 417-447.

Klempner et al, Interpenetrating Polymer Networks, Advances in Chemistry; American Chemical Society, 1994, 21-38.

Dolas RT et al, Raft Technology for Gatsro Retentive Drug Delivery, Human Journal, 2015, 3(1):232-252.

Prajapati VD et al, Raft forming system—An upcoming approach of gastroretentive drug delivery system, Journal of Controlled Release, 2013, 168(2):151-165.

Davis SS et al., Transit of Pharmaceutical Dosage Forms Through the Small Intestine, Gut, 1986, 27(8):886-892.

Broughton et al., Gamma-hydroxy-butyrate in the treatment of narcolepsy: a preliminary report, In: Guilleminault et al. (Eds.).

Narcolepsy (Advances in sleep research. vol. 3.). Holliswood, NY: Spectrum Publications, pp. 659-667, Jan. 1976.

Flamel Technologies Announces Positive Results of a Second Clinical Trial with Micropump® Sodium Oxybate, Dec. 19, 2014, which reports achieving the objective of one single dose before bedtime.

Frucht et al., A Pilot Tolerability and Efficacy Trial of Sodium Oxybate in Ethanol-Responsive Movement Disorders, Movement Disorders, vol. 20(10):1330-1337, Jun. 2005.

Mamelak et al., The effects of [gamma]-hydroxybutyrate on sleep, Biol Psychiatry, vol. 12(2):273-288, Aug. 1976 (published 1977).

Patil, J. S. et al. Ionotropic Gelation and Polyelectrolyte Complexation: the Novel Techniques to Design Hydrogel Particulate Sustained, Modulated Drug Delivery System: a Review *Digest Journal of Nanomaterials and Biostructures,* Mar. 2010, 5(1):241-248.

Arora S et al., Floating Drug Delivery Systems: A Review, AAPS PharmScieTech, 2005, 6(3):E372-E390.

Chen Y et al., Cubic and Hexagonal Liquid Crystals as Drug Delivery Systems, BioMed Research International, 2014:1-12.

Jain D et al., Recent technologies in pulsatile drug delivery systems, Biomatter, 2011, 1(1):57-65.

Kumar KK et al., Formulation and evaluation of floating in situ gelling system of losartan potassium, Der Pharmacia Lettre, 2015, 7(1):98-112.

Lam WK et al., Monocarboxylate Transporter-Mediated Transport of Gamma-Hydroxybutyric Acid in Human Intestinal Caco-2 Cells, Drug Metabolism and Disposition, 2010, 38(3):441-447.

Liechti ME et al., Pharmacokinetics and pharmacodynamics of gamma-hydroxybutyrate in healthy subjects, British Journal of Clinical Pharmacology, 2016, 81:980-988.

Madan JR et al., Development and evaluation of in situ gel of pregabalin, International Journal of Pharmaceutical Investigation, 2015, 5(4):226-233.

Patel DM et al., Formulation and Evaluation of Floating Oral In Situ Gelling System of Amoxicillin, ISRN Pharmaceutics, 2011.

Sajan J et al., Chromotherapeutics and Chronotherapeutic Drug Delivery Systems, Tropical Journal of Pharmaceutical Research, 2009, 8(5):467-475.

Vijaya C and Goud KS, Ion-activated In Situ Gelling Ophthalmic Delivery Systems of Azithromyin, Indian Journal of Pharmaceutical Sciences, 2011, 73(6):615-620.

Saito S et al., Combination of borane-dimehtyl sulfide complex with catalytic sodium tetrahydroborate as a selective reducing agent for alpha-hydroxy esters, versatile chiral building block from (s)-(-)-malic acid, Chemistry Letters, 1984, 1984:1389-1392.

Singh, I. et al. Ion Exchange Resins: Drug Delivery and Therapeutic Applications *FABAD J. Pharm. Sci.,* Jul. 2006, 32:91-100.

Jain, U.S. Appl. No. 16/955,377, filed Jun. 18, 2020.

Jain, U.S. Appl. No. 16/955,389, filed Jun. 18, 2020.

Jain, U.S. Appl. No. 16/955,373, filed Jun. 18, 2020.

International Search Report and Written Opinion issued Apr. 2, 2019 in International Patent Application No. PCT/US2018/066299.

International Search Report and Written Opinion issued Apr. 15, 2019 in International Patent Application No. PCT/US2018/066300.

International Search Report and Written Opinion issued Apr. 3, 2019 in International Patent Application No. PCT/US2018/066301.

International Search Report and Written Opinion issued Apr. 3, 2019 in International Patent Application No. PCT/US2018/066303.

Non-Final Office Action, dated Nov. 10, 2021, issued in U.S. Appl. No. 16/955,373 and Response dated Nov. 10, 2021.

Non-Final Office Action, dated Jul. 7, 2021, issued in U.S. Appl. No. 16/955,377, and Response dated Jan. 7, 2022.

Notice of Allowance issued in U.S. Appl. No. 16/955,377, dated Feb. 3, 2022.

Non-Final Office Action, dated Jun. 30, 2021, issued in U.S. Appl. No. 16/955,392 and Response dated Dec. 30, 2021.

Notice of Allowance, dated Jan. 26, 2022, issued in U.S. Appl. No. 16/955,392.

Office Action issued in European Patent Application No. 18834152.3, dated May 14, 2021, and Response dated Nov. 22, 2021.

Office Action issued in European Patent Application No. 18834153.1, dated May 14, 2021, and Response dated Nov. 19, 2021.

(56) References Cited

OTHER PUBLICATIONS

Office Action issued in European Patent Application No. 18840118.6, dated May 31, 2021, and Response dated Dec. 10, 2021.
Non-Final Office Action, dated Nov. 7, 2023, issued in U.S. Appl. No. 17/725,673.
Non-Final Office Action, dated Mar. 21, 2022, issued in U.S. Appl. No. 16/955,389, and response.
Final Office Action, dated Sep. 16, 2022, issued in U.S. Appl. No. 16/955,389, and response.
Office Action issued in European Patent Application 18834152.3, dated Nov. 10, 2022, and response.
Office Action issued in Israeli Patent Application 275312, dated Dec. 1, 2022, and response.
Office Action issued in European Patent Application 18840118.6, dated Nov. 10, 2022, and response.
Office Action issued in Chinese Patent Application 201880089838.9, dated Feb. 28, 2023.
Office Action issued in Israeli Patent Application 275444, dated Dec. 11, 2022, and response.
Office Action issued in European Patent Application 18834153.1, dated Nov. 10, 2022, and response.
Office Action issued in Japanese Patent Application 2020-554387, dated Oct. 12, 2022.
Office Action issued in Canadian Patent Application 3,097,737, issued Sep. 27, 2023, and response.
Office Action issued in European Patent Application 18834152.3, dated Nov. 24, 2023.
Office Action issued in Canadian Patent Application 3,085,941, issued Sep. 27, 2023, and response.
Office Action issued in European Patent Application 18840118.6, dated Dec. 5, 2023.
Office Action issued in Israeli Patent Application 275444, dated Jan. 30, 2024.
Final Rejection issued in Japanese Patent Application 2020-554387, dated Jun. 2, 2023.
Office Action issued in European Patent Application 18834153.1, dated Nov. 24, 2023.
Office Action issued in Canadian Patent Application 3,086,153, issued Sep. 27, 2023, and response.
Examination Report issued in Australian Patent Application 2018388577, issued Nov. 8, 2023.
Office Action issued in Chinese Patent Application 201880089838.9, dated Aug. 23, 2023.
Office Action issued in Chinese Patent Application 201880089838.9, dated Jan. 10, 2024.
Office Action, dated May 20, 2022, issued in U.S. Appl. No. 16/955,373.
Non-Final Office Action, dated Dec. 16, 2022, issued in U.S. Appl. No. 16/955,373, and response.
Office Action, dated Aug. 16, 2023, issued in U.S. Appl. No. 16/955,373, and response.
Non-Final Office Action, dated Dec. 28, 2023, issued in U.S. Appl. No. 16/955,373.
Notice of Allowance issued in Israeli Patent Application 275312, dated Jan. 23, 2024.

* cited by examiner

PHARMACEUTICAL COMPOSITION COMPRISING GHB GASTRO-RETENTIVE RAFT FORMING SYSTEMS HAVING TRIGGER PULSE DRUG RELEASE

CROSS-REFERENCE TO RELATED APPLICATIONS

This application is a continuation of U.S. patent application Ser. No. 16/955,392, filed Jun. 18, 2020, which claims the benefit of priority of International Patent Application No. PCT/US2018/066299, filed Dec. 18, 2018, which claims priority to U.S. Provisional Patent Application No. 62/607,159, filed Dec. 18, 2017. These applications are incorporated by reference herein.

BACKGROUND OF THE INVENTION

Some drug molecules exhibit site specific absorption from upper part of small intestine. These molecules exhibit faster and greater absorption in the upper part of the GI tract (stomach, duodenum and jejunum) and slower and lesser absorption in the lower part of the GI tract (ileum, colon and rectum). For such molecules, traditional long acting liquid dosage forms are likely to show lower bioavailability due to incomplete absorption as the dosage form is likely to transit before completing the drug release and prior to absorption. WO2016087952 A1 relates to a gastro-retentive extended release suspension composition, wherein the composition is reportedly characterized by having no substantial change in the in-vitro dissolution release profile upon storage for at least seven days. The extended release (ER) suspension discussed therein contains an osmogent. The hypertonic condition generated in the suspension base affects the leaching of the active ingredient from the extended release coated cores into the suspension base. Reportedly, this hypertonic condition minimizes leaching of the drug from the ER component and thus provides substantially similar in-vitro extended release of the active ingredient throughout the shelf life of the composition Gastroretentive drug delivery systems based on floating rafts have been described in the literature. Certain raft systems are floating, which contain a polymer and gas generating agent, designed to delay clearance of the raft system from the stomach. Different raft forming approaches discussed in the prior art include: swelling based raft formation, temperature dependent gelling based raft formation, pH dependent gelling agent based raft formation, ionic cross-linking based raft formation [Pawar Ashish Yashwantrao et al, A Raft forming system: A Novel approach for gastro-retention, Int. J. Pure App. Biosci. 3 (4): 2015 (178-192).] However, Raft formation has been applied in drug delivery field with limited success, especially limited success when applied to drug molecules that exhibit site specific absorption in upper part of GI tract and at least one of the following: saturable first pass metabolism in GI tract and liver, very short elimination half-life (<3 hours), used for treating diseases following biological rhythms in the form of long acting liquids.

Sodium GHB is highly water-soluble, hygroscopic and strongly alkaline. See, e.g., WO2011/119839. Despite its high water solubility, it forms a gel when dissolved in water. See, e.g., U.S. Pat. No. 8,193,211, also published as US Patent Application US 2006/0210630 A 1. These properties, along with the large amount of the drug that is required to achieve the clinical effect, present challenges in preparing solid unit dosage forms that are designed for immediate release of the sodium GHB into the gastrointestinal tract of the user. See, also, U.S. Pat. No. 8,193,211.

U.S. Pat. No. 8,193,211 describes administration of GHB using pulsed type dosage form, i.e., an immediate release component and a delayed/controlled release component. The immediate release component is described as being an aqueous solution, or a "solid pellet, bead or mini tablet." While the pellets disclosed in Example 1 comprise as much as 80-90 wt % sodium GHB, they are the immediate release portion of the controlled release dosage form and are not formed into a compressed tablet. These immediate release components of GHB are combined with one or more delayed/controlled release components of GHB.

US Patent Publication 2012/0076865 describes a controlled release dosage form for oral administration containing at least one GHB drug, wherein less than 30% of the at least one drug is released during the first hour after administration. The at least one drug is selected from GHB and pharmaceutically acceptable salts, hydrates, tautomers, solvates and complexes thereof.

Flamel has described use of its Micropump®-based technology with sodium GHB for narcolepsy. See, e.g., "Flamel Technologies Announces Positive Results of a Second Clinical Trial with Micropump® Sodium Oxybate", Dec. 19, 2014, which reports achieving the objective of one single dose before bedtime.

The use of drug-ion exchange resin complexes to provide controlled release of active agents has been described. See, e.g., US 2007/0036843 and documents cited therein. This document identifies over 225 possible drugs which may be loaded onto, or bound, to an ion exchange resin, but provides only a couple of working examples. WO2015/166473 reports that ion exchange resin technology is not suitable for many active ingredients.

There continues to be a need for safe, effective and improved patient compliant pharmaceutical formulations for GHB.

SUMMARY OF THE INVENTION

The present invention provides a GHB composition which can generate two pulses of drug release, first pulse immediately after administration and second pulse 2 to 6 hours after the first pulse, while retaining the dosage form in upper part of GI tract for a longer period of time.

In one aspect, an orally administrable drug powder GHB composition is provided which forms a gastro-retentive RAFT having at least two trigger pulses. The composition comprises: (a) at least one drug in a first pulse; (b) at least one drug in a delayed trigger release form; and (c) a RAFT system provided that the at least one drug of (a) and/or (b) comprises a GHB drug(s). Optionally, in addition to comprising at least one GHB drug(s), a second biologically active moiety may be included in the composition. Following oral ingestion, the composition provides a self-assembling gastro-retentive RAFT having entrapped therein, the at least one drug of (a) and (b) and the gas generated in situ by the non-toxic gas generating agent, thereby providing a floating gastro-retentive RAFT having a dual pulse system wherein at least the second pulse is a trigger pulse and which retains the at least one drug in the stomach for at least about 3 hours.

In certain embodiments, the composition comprises at least one GHB drug in a first pulse and at least one GHB drug in a pH sigmoidal delayed trigger system. The trigger pulse system comprises (a) at least one drug, and/or -drug-ion exchange resin complex; an organic acid coated with a reverse enteric coat; an optional gas generating agent; an optional bulking agent; and (b) coat comprising at least one pH-independent, water-insoluble, water-permeable diffusion barrier coating polymer, e.g., Ammonio Methacrylate Copolymer, Type A (e.g., Eudragit® RL), and Ammonio Methacrylate Copolymer, Type B (e.g., Eudragit® RS)) over the particles of (a), wherein said coat dissolves in the presence of the organic acid of (a), whereby following ingestion in the presence of acid a RAFT comprising a pH sigmoidal delayed trigger for the drug of (a) is formed.

In certain embodiments, the composition comprises at least one GHB drug in a first pulse and at least one GHB drug in an erosion delayed trigger system. Such a trigger release system comprises: at least one erosion barrier forming polymer; an optional gas generating agent; at least one drug and/or drug-ion exchange resin complex; and an optional bulking agent, whereby in the presence of stomach acid, a RAFT comprising the erosion delayed trigger system for the drug is formed.

In certain embodiments, the composition comprises at least one GHB drug in a first pulse and at least one GHB drug in a pH, swelling delayed trigger system. Such a trigger system comprises: (i) granules comprising at least one pH modifier, at least one swelling agent coated with at least one enteric polymer, (ii) granules of step (i) optionally further coated with reverse enteric coat (e.g.,) whereby in the presence of stomach acid, a RAFT comprising the pH-swelling delayed trigger system for the drug of (i) is formed.

In certain embodiments, the composition at least one GHB drug in a first pulse and at least one GHB in a swelling delayed trigger system. This trigger system comprises: (i) granules comprising at least one drug and/or drug-ion exchange resin complex, at least one gelling agent, at least one swelling enhancer, an optional gas generating agent which generates gas in the presence of stomach acid, optionally, a bulking agent, and (ii) at least one water permeable diffusion barrier coating over the granules of (i), whereby in the presence of stomach acid, a RAFT comprising the swelling delayed trigger system for the drug of (i) is formed.

In certain embodiments, use of a gastro-retentive RAFT forming composition having at least one drug in a first pulse and at least one drug in a trigger pulse release for treating a patient is provided. In a further embodiment, a method of treating a patient having chronic fatigue syndrome, cataplexy, sleep apnea, Parkinson's disease, schizophrenia, binge eating, essential tremor and non-Parkinsons's movement disorders, chronic cluster headache, and/or reducing constipation associated with opioids and opioid-related drugs is provided. The method comprises providing said patient with a therapeutically effective amount of a composition as described herein.

In another aspect, a kit for treating a patient with a GHB drug is provided.

These and other advantages of the present invention will be apparent from the following detailed description of the invention.

BRIEF DESCRIPTION OF THE INVENTION

Figure 1B:
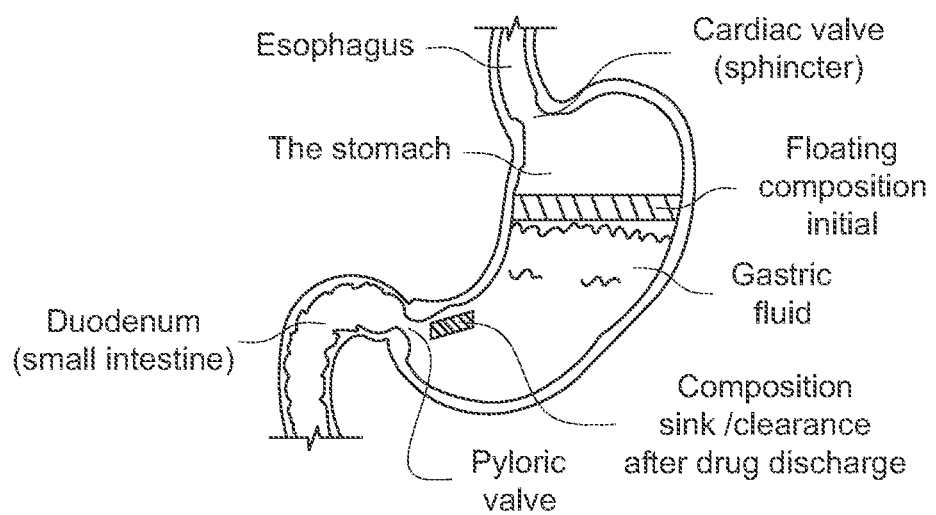

FIGS. 1A and 1B provide schematics of the human gastrointestinal system. FIG. 1A provides an overview of the digestive system, including the stomach, duodenum and jejunum. FIG. 1B provides an enlarged schematic of the stomach, illustrating the entry to the stomach from the esophagus and the exit from the stomach through the pyloric valve into the duodenom. Within the stomach, the floating of the RAFT on the gastric fluid is illustrated at different times post-administration, including "floating" and when it "sinks" following drug release in order to clear through the pyloric valve.

Figure 2:
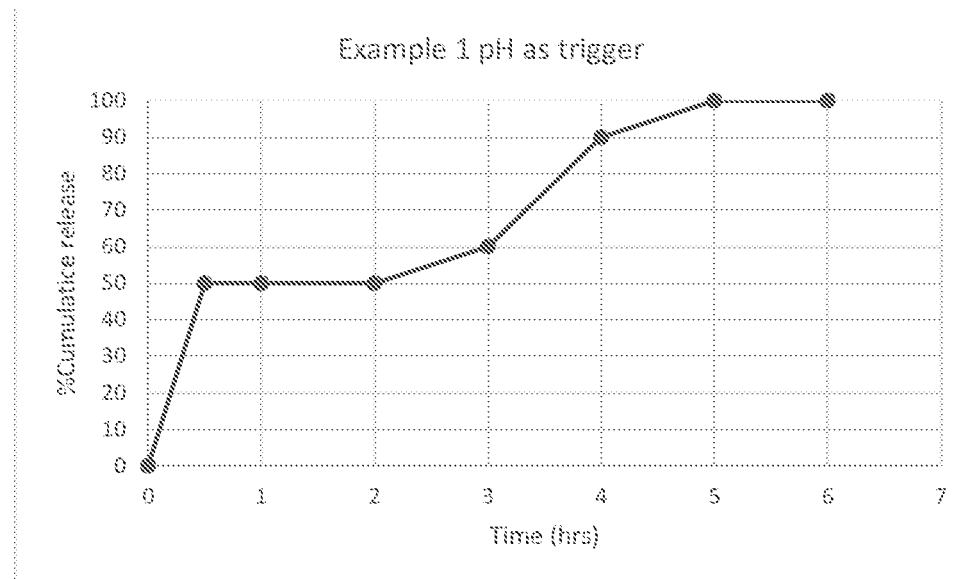

FIG. 2 provides the anticipated dissolution profile from the GHB drug composition of Example 1, as assessed over 6 hours. The percentage (%) cumulative release is shown for the composition which comprises pH as the trigger pulse.

Figure 3:
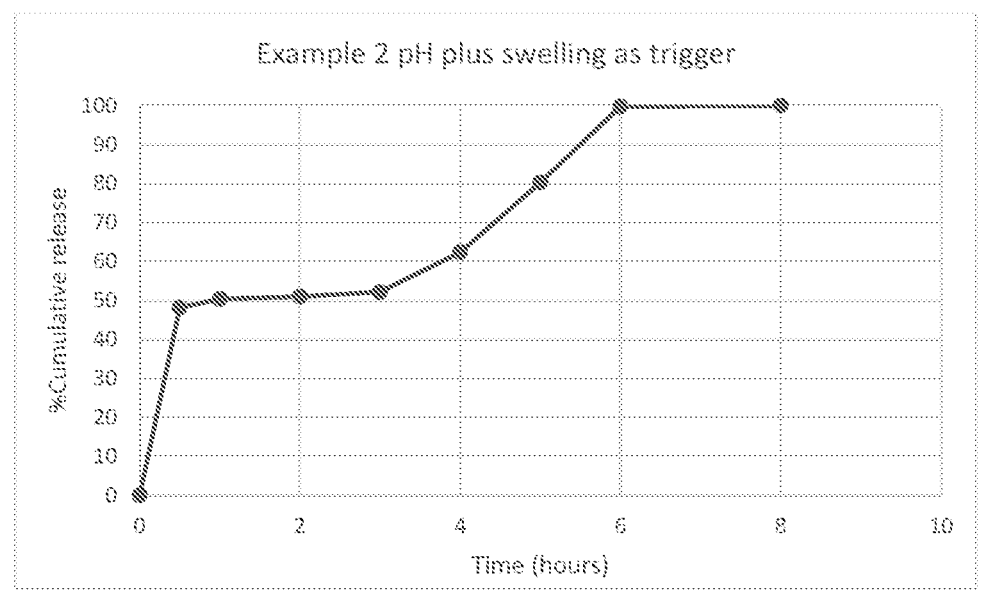

FIG. 3 provides the anticipated dissolution profile from the GHB drug composition of Example 2, as assessed over 8 hours. The percentage (%) cumulative release is shown for the composition which comprises pH plus swelling as the trigger pulse.

Figure 4:
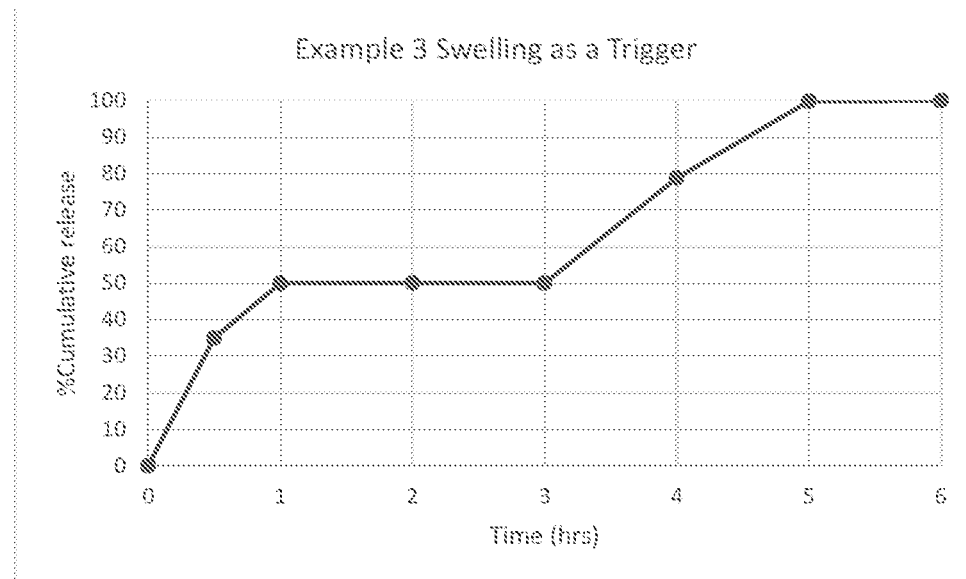

FIG. 4 provides the anticipated dissolution profile from the GHB drug composition of Example 3, as assessed over 6 hours. The percentage (%) cumulative release is shown for the composition which comprises swelling as the trigger pulse.

Figure 5:
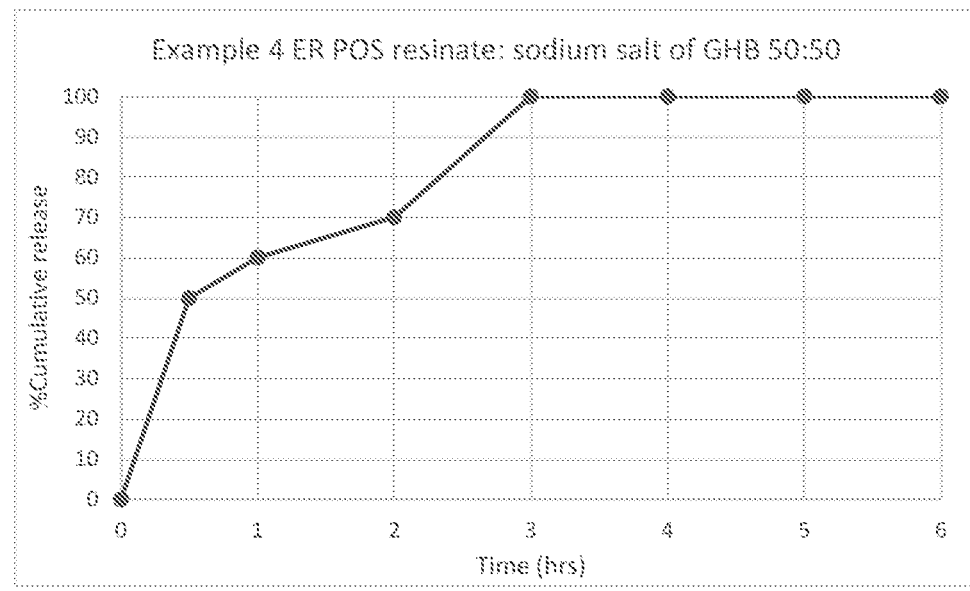

FIG. 5 provides the anticipated dissolution profile from the extended release (ER) GHB powder for suspension (POS) composition of Example 4, as assessed over 6 hours. The percentage (%) cumulative release is shown for the composition which comprises a GHB-drug ion exchange resin complex and sodium oxybate (sodium salt of GHB) in a 1:1 ratio (50:50).

DETAILED DESCRIPTION OF THE INVENTION

A gastro-retentive (GR) pulse release (PR) composition as provided herein may be a powder which, post-dosing, provides at least two pulse releases of one or more GHB drug(s). The compositions may be reconstituted with water at the time of administration to form suspension or paste or pudding, which might be filled into capsule.

"A GHB drug" includes, GHB, as well as pharmaceutically acceptable salts, hydrates, tautomers, solvates, prodrugs and complexes of GHB, and mixtures thereof. Suitable salts of GHB include, e.g., the calcium, lithium, potassium, sodium and magnesium salts. Representative salts are also described in US 2012/0076865, incorporated by reference herein. The sodium salt of GHB, "sodium oxybate", refers to a compound of formula (Ia):

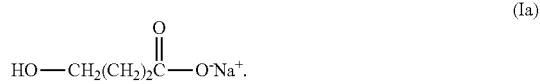

In one embodiment, an alternative to the sodium oxybate may be used as the immediate release component, or as the starting material to prepare a drug-ion exchange resin complex" refers to the product resulting as provided herein. Such alternative salts useful in the present invention include compounds of formula (I):

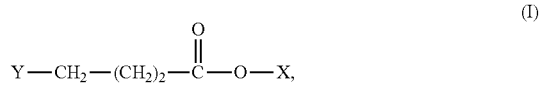

wherein X is a pharmaceutically-acceptable cation and may be selected from loading at least one drug onto an ion exchange resin. The group consisting of potassium, calcium, lithium and magnesium and Y is OH. By "oxybate salt" is intended a compound of formula I wherein X is a pharmaceutically-acceptable cation and may be selected from the group consisting of sodium, potassium, calcium, lithium and magnesium and Y is OH. Sodium gamma-hydroxybutyrate (GHB) is currently available from Jazz Pharmaceuticals, Inc. as Xyrem® oral solution. Sodium oxybate is a white to off-white, crystalline powder that is very soluble in aqueous solutions. Other salts may be selected, such as calcium oxybate, magnesium oxybate, potassium oxybate, and/or lithium oxybate. Methods for preparing such complexes have been of making GHB salts are described, e.g., for example, in WO 2007/109104 and US 2007/0215511A1, U.S. Pat. No. 4,393,236, the disclosure of which is incorporated herein by reference.

One exemplary prodrug is 3-hydroxy-γ-butyrolactone. See, e.g., U.S. Pat. No. 6,713,693, which describes a process for preparing enantiomerically pure (S)-3-hydroxy-gamma butyrolactone, the disclosure of which is incorporated by reference herein. (S)-3-hydroxy-γ-butyrolactone can also be obtained from the selective reduction of (L)-malic acid ester (U.S. Pat. No. 5,808,107, the disclosure of which is incorporated by reference herein; Chem. Lett. 1984, 1389).

Such GHB drugs may be in an unaltered state (e.g., free API or a salt thereof) or in the form of a particle, granule, complex, optionally containing excipients, or mixtures thereof. It will be understood that unless otherwise specified, more than one GHB drug may be used. By way of non-limited example, a combination of GHB salts may be used rather than a single GHB salt as the "free API"). In certain embodiments, in addition to the at least one GHB drug(s) (e.g., gamma hydroxybutyrate or its salts, hydrates, tautomers, or solvates, or complexes thereof, or mixtures thereof), the composition contains at least one additional biologically active moiety. In certain embodiments, the compositions may include, 0.1 mg to 20 g of active drug(s).

In certain embodiments, the GHB drug(s) alone or in combination with at least one additional biologically active moiety is about 0.1 w % to 90 wt %, more preferably about 1 wt % to 75 wt %, or about 15 wt % to 60 wt % based on the total weight of the final dosage form. Unless otherwise specified, when the weight percentage of a complexed GHB or other drug is provided, it is based on the weight of the free base of the drug, unless the pharmaceutically acceptable salt form thereof, is provided. For example, the weight percentage of GHB in a drug-ion exchange resin complex is based on the weight contributed by the GHB, exclusive of any ion exchange resin, polymer, coating, or other component.

A "drug-ion exchange resin complex" refers to the product resulting from loading at least one drug onto an ion exchange resin. In certain embodiments, this describes the complexation which occurs when the active drug(s) and the ion exchange resin are mixed together in an aqueous medium to facilitate the "exchange" between a salt of the drug and the "ion" of the ion exchange resin and the formation of the complex. Unless otherwise specified, a drug-ion exchange resin complex may be uncoated or coated. When in a drug-ion exchange resin complex, a GHB is bound to an anion exchange resin, such as described in more detail below. Other drugs, e.g., modafinil or nalmefene, which may be used in combination or co-therapy with a GHB drug(s) may be bound to a cation exchange resin. In certain embodiments, modafinil may additionally or alternatively complex to an anion exchange resin. Methods for preparing drug-ion exchange complexes have been described, e.g., in WO 2007/109104 or US 2007/0215511, incorporated herein by reference. Optionally, a drug-ion exchange resin complex may contain more than one drug bound thereto. Additionally, or alternatively, compositions provided herein, may contain two different drug-ion exchange resin complexes.

As used herein, the term "biologically active moiety" or "biologically useful moiety" for use in combination with a GHB drug(s) or in co-therapy therewith, may include an "active pharmaceutical ingredient" or "API", a nutraceutical, a vitamin or other desired moiety. For example, such a drug may be modafinil (e.g., for treating narcolepsy), nalmefene (e.g., for use in treating alcohol dependency or abuse) and may be administered in immediate release or modified release form, within the floating IPN, in the composition but outside of the floating IPN, or administered by a different route as a co-therapy. These or another drug(s) for use in combination or co-therapy with the GHB drug of the composition is selected is one which, when administered outside of the composition of the invention, has more rapid clearance from the stomach and, optionally other parts of the gastrointestinal tract than is desired. Thus, the composition of the invention can provide a modified release profile to a drug and increased bioavailability. This is particularly desirable for drugs which are to be targeted to the gastrointestinal tract (particularly the stomach). However, this is not a limitation on its utility.

As used herein, an "API" is any substance or mixture of substances intended to be used in the manufacture of a drug product and that, when used in the production of a drug, becomes an active ingredient in the drug product. Thus, an API may be, e.g., one or more small molecule drugs, cancer therapeutics, or biologics (e.g., hormones, enzymes, peptides, polypeptides, antibodies, antibody fragments, single domain antibody, etc)). Small molecule drugs are generally under about 900 daltons in molecular weight and may be a free base or acid drug or a pharmaceutically acceptable salt, solvate, or hydrate, thereof. In certain embodiments, a biologically useful moiety is in a particle or granule. In certain embodiments, such particles or granules may contain one or more drug-ion exchange resin complexes. In certain embodiments, such particles or granules contain excipients. In certain embodiments, such biologically active moieties (and/or complexes, particles or granules containing same) may be uncoated, or coated with a modified release coating. Unless otherwise specified, where the term "drug" is used in this specification, another biologically active moiety may be substituted. It will further be understood that unless otherwise specified, more than one drug may be used.

In certain embodiments, a GR PR composition as provided herein generates a first pulse of drug release within about three hours post-dosing of the composition and at least a second pulse of the drug about 2 hours to about 6 hours after the first pulse.

The term "gastro-retentive" or "GR" as used herein, means post-dosing (e.g., by oral ingestion) at least a portion of the dosed composition remains in the stomach for a period that is longer than the normal emptying time from the stomach, i.e., at least about 2 hours and up to about 24 hours, at least about 3 hours to up to about 24 hours, about 4 hours to about 16 hours, about 5 hours to about 12 hours, or about 6 hours to about 8 hours. Examples of suitable assays for assessing the period of gastric retention are described the examples herein, including the assays for onset and duration of floating in simulated gastric fluid (SGF) without enzyme and integrity/resiliency in SGF. Additionally, a gamma-scintigraphy study may be performed in humans to actually visualization of retention of dosage form in stomach (& upper GIT) along with time for which it remains there will be evaluated. SS Davis, et al, Alimentary tract and pancreas Transit of pharmaceutical dosage forms through the small intestine Gut, 1986, 27, 886-892.

As used herein, a "pulse" refers to a drug release system in which a predetermined amount of a drug is released in a manner that a complete and rapid drug release follows a lag time.

As used herein, a "powder for suspension" or "POS" refers to a composition which is formulated as a powder which designed to be suspended in a suspension base prior to oral ingestion by a patient.

In certain embodiments, the gastro-retentive pulse release (GRPR) POS is particularly well suited for use with a biologically active moiety: (i) that exhibits site specific absorption in upper part of GI tract and saturable metabolism in GI tract and liver; (ii) that exhibits site specific absorption in upper part of GI tract and very short elimination half-life (<3 hours), and/or (iii) that exhibit site specific absorption in upper part of small intestine and are used for treating diseases following biological rhythms. However, other suitable biologically active moieties useful in the invention are described herein and/or will be apparent to one of skill in the art based on the following description.

As used in the preceding paragraph and throughout the specification, the "upper part of the GI tract" for absorption includes the stomach, duodenum and jejunum.

In general, API having solubility or stability problems in the pH conditions of the stomach (under pH 4) are not suitable for the compositions described herein. However, certain uncomplexed drugs may be designed in a drug-ion exchange resin complex, or in a granule, particle or other form as described herein which addresses these solubility or stability issues.

The trigger release mechanisms described herein may be used in combination with a variety of raft forming systems and/or the novel floating IPN forming system described in detail in a US provisional patent application entitled, "GHB Pharmaceutical Compositions Comprising a Floating Interpenetrating Polymer Network Forming System", which is being filed on the same date herewith and which is incorporated herein by reference in its entirely. Such raft systems are described in more detail below.

Pulse Release (PR) of Moiety from GR POS

In certain embodiments, the GHB compositions provided herein are designed to have at least two pulses of at least one GHB drug(s), a first pulse and at least a second pulse which is a trigger pulse comprising at least one GHB drug(s). In certain embodiments, only one pulse comprises GHB drug(s). Optionally, one or more pulses may contain, in addition to GHB drug(s), a second, different drug for use in combination with the GHB drug(s), further, the composition may provide more than one pulse releases. Suitably, the ratio of amount of drug(s) in the first pulse:amount of drug(s) in the second pulse can be from 2:98 to 85:15, based on the weight of the active moiety in its free form (i.e., without including the weight of any salt or complex component). In certain embodiments, the ratio may be about 1:10 to about 10:1, or about 1:1, about 1:20, about 2:1, about 1:4, about 4:1. Values therebetween may be readily selected.

In certain embodiments, the compositions provided herein may have three, or more pulses. In such embodiments, typically the first pulse is instant and at least one other pulse is the trigger release pulse as described herein. In certain embodiments, the compositions provide at least two pulses of the same drug. In other embodiments, the compositions provide two or more drugs, which may be included in at least a first pulse or at least a second pulse. In such instances, the timing of an at least second pulse is determined relative to the timing of a first pulse of the same drug.

A first pulse, as in the instant compositions, may be essentially instantly post-dosing. In certain embodiments, a composition as provided herein provides a drug with a first pulse corresponding to about 10 to about 80% of total dose is formulated as free drug(s) (e.g., sodium oxybate or a mixture of oxybate salts), a drug-ion exchange resin complex, and/or a mixture thereof. As described herein, the compositions are designed to provide a first pulse within about 3 hours post-dosing, or within about 2 hours post-dosing, or within about 1-hour post-dosing (e.g., about 10 minutes to 60 minutes).

Compositions provided herein provide at least a second pulse, which uses a trigger mechanism. In certain embodiments, a composition as provided herein provides a drug with the at least second pulse corresponding to about 20 to about 90% of total dose is formulated as trigger principle. Different trigger mechanisms are used for releasing second pulse of API about 2 hours to about 6 hours after the first pulse. The second pulse contain can be achieved by using free drug(s), a drug-ion exchange resin complex, and/or a mixture thereof.

Suitable trigger mechanisms include (a) pH as Trigger: sigmoidal release system, (b) erosion as trigger, (c) pH plus swelling as Trigger for generating second pulse, (d) swelling as pulse, combinations of these systems, and/or combinations of one or more of these systems with other trigger systems such as are identified herein. Such systems are described in more detail below.

It will be noted that for the "first pulse", a biologically active moiety may be provided in any form which is suitable for release in less than about 3 hours, and in certain embodiments, for release in less than about 2 hours, or less than about 1 hour. In certain embodiments, the moiety (e.g., a drug) is delivered as a free base or acid API, or a pharmaceutically acceptable salt thereof. In certain embodiments, the moiety is in a drug-ion exchange complex without a modified release coating. In certain embodiments, the moiety for the first pulse is in a particle, granule, or layered onto a sphere, in the absence of a modified release coating.

Additionally, the compositions provided herein contain at least one biologically active moiety in at least a second pulse form. The following paragraphs describe suitable trigger pulse releases for the at least second pulse forms in the compositions.

As provided herein, a "gas generating agent" refers to an agent that generates nontoxic gas upon contact with gastric fluid. Suitable gas-generating agents include, without limitation, carbonates or bicarbonates of an alkali or alkaline earth metal, such as potassium carbonate or potassium bicarbonate, sodium carbonate or sodium bicarbonate, calcium carbonate, sodium glycine carbonate, magnesium carbonate, and aluminum carbonate; and sulfites such as sodium sulfite, sodium bisulfite, and sodium metabisulfite. These salts may be used alone or in combination with an acid source as a gas-generating couple. The final compositions provided herein include a gas generating agent. The gas generating agent may be present in one or more of the trigger pulse system, the raft forming composition, or admixed with one or more of the other components in the composition. In general, once the gas is entrapped in the GR raft, floating continues as long as integrity of the raft is retained. Thus, same concentration of gas which works for 3-hour (hr) floating is also suitable for longer time periods, e.g., a 12 hr float. In certain embodiments, a gas generating agent is present in concentration range of about 1 w/w to about 25 w/w of the total weight of the GR raft. Suitably, the gas generating agent provides rapid onset (less than about 15 min) and at least or greater than about 3 hr floating. Float may be assessed in vitro using a suitable assay such as those described herein, e.g., in 500 ml simulated gastric fluid without enzymes, and/or other assays known in the art.

Suitably, the GR raft provides at least a GHB drug(s) with a period of retention in the stomach which is longer than the period of time which the moiety would have if administered directly. In certain embodiments, this results in increase bioavailability, absorption, and/or activity in the "gastrointestinal tract" including, the stomach, duodenum, and/or jejunum.

Swelling as Trigger

In certain embodiments, a composition contains at least one GHB drug and (i) at least one gelling agent selected from hydrogel forming polymers; (ii) at least one swelling enhancer selected from the following non-limiting list of super-disintegrants; (iii) at least one water permeable diffusion barrier coating; (iv) optionally a gas generating agent; and (v) optionally, a bulking agent, e.g., microcrystalline cellulose (MCC), including e.g., silicified MCC, mannitol, among others.

Granules comprising at least one drug(s) (e.g., GHB, a GHB-ion exchange resin complex, oxybate salt, or mixtures thereof, optionally with a different drug), gelling agent and swelling enhancer are coated with the diffusion barrier. Without being bound by any theory, it is believed that upon coming into contact with aqueous medium; swelling enhancer causes rapid water uptake. Gelling agent starts forming hydrogel and swelling and starts pushing the coat. Relative proportions of core excipients and coat thickness are optimized such that coat is removed completely due to swelling after 2 and before 6 hrs. Onset of second pulse is tailored by modifying the relative proportions of swelling enhancer and gelling agent and; by modifying the coat thickness. Higher proportion of swelling enhancer and lower portion of gelling agent ensures rapid drug release once coat is removed.

One or more gelling agents are selected from non-limiting list of hydrophilic polymers which form a hydrogel in aqueous medium: carbomers, guar gum, xanthan gum, gum arabic, tragacanth, cellulose polymers and their derivatives (such as, e.g., hydroxypropylmethylcellulose (HPMC), hydroxypropyl cellulose, methylcellulose, and hydroxyethyl cellulose (HEC), carboxymethylethyl cellulose, hydroxyethylmethyl carboxymethyl cellulose, hydroxyethyl methyl cellulose, carboxymethyl cellulose, methylhydroxyethyl cellulose, methylhydroxypropyl cellulose or any mixtures thereof), polysaccharides and their derivatives, polyalkylene oxides, polyethylene glycols, chitosan, poly(vinyl alcohol), xanthan gum, maleic anhydride copolymers, starch-based polymers, crosslinked polyacrylic acids, and combinations thereof.

One or more at least one swelling enhancer, for example, super-disintegrant is selected from non-limiting list of super-disintegrants: crospovidone, SSG, crosslinked sodium carboxymethylcellulose. Swelling enhancer promotes rapid absorption of large amount of aqueous fluid.

At least one water permeable diffusion barrier coating covering the granules comprising API, gelling agent and swelling enhancer. In certain embodiments, the barrier coating adds about 5% w/w to about 80% w/w to the coated granules.

Diffusion barrier coating contains at least one diffusion barrier forming polymer system. Suitable barrier coatings include but are not limited to, water-insoluble release modifiers or water-soluble release modifiers or combinations thereof. The water-insoluble release modifiers that may be employed include polymeric water-insoluble release modifier or non-polymeric water-insoluble release modifier or combinations thereof. Suitable polymeric water-insoluble release modifiers include, but are not limited to, cellulose polymers and derivatives thereof, polyacrylic acid and polymethacrylic acid polymers and derivatives thereof, maleic acid copolymers and derivatives thereof, polyvinyl derivatives; and the like or any combinations thereof. In one embodiment, suitable polymeric water-insoluble release modifiers include, but are not limited to, polyvinyl acetate, polyvinyl chloride, polyvinyl carbonate, ethyl cellulose, nitrocellulose, vinylidene chloride-acrylonitrile copolymer, acrylonitrile-styrene copolymer, ethylene vinyl acetate, cellulose acetate, cellulose acetate phthalate, cellulose acetate butyrate, copolymers of vinyl pyrrolidone, blend of polymers comprising polyvinyl acetate, hydroxypropyl methylcellulose phthalate, methacrylic acid copolymers such as Eudragit® L100/S100/L100-55 and the like or mixtures thereof; methacrylate copolymers such as Eudragit® E100/EPO, Eudragit® RL100/RL30D/RLPO, Eudragit® RS100/RS30D/RSPO and the like or mixtures thereof. Suitable non-polymeric water-insoluble release modifiers include, but are not limited to, fats, oils, waxes, fatty acids, fatty acid esters, glycerides, long chain monohydric alcohols and their esters, phospholipids, terpenes or combinations thereof. Suitable release modifiers in each of these categories have been listed hereinbefore.

In one embodiment, the barrier coating is a pH-independent, water insoluble, water-permeable barrier coating which optionally contains one or more plasticizers, and which is optionally cured. Optionally, the coating includes a plasticizer is used in the percent range, or a mixture of plasticizers combine to total, about 2 to about 50% by weight of the coating layer, more preferably about 2.5% to about 20% by weight of the coating layer on the coated drug-ion exchange resin complex. Preferably a plasticizer in range of about 5% to about 10% by weight of the coating layer based on the coated complex provides the most desirable properties. Suitable plasticizers are water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor P, and mixtures thereof. Other plasticizers are described in Patent Application Publication No. US 2003/0099711 A1, May 29, 2003, page 4 (0041) the disclosure of which is incorporated herein by reference.

In certain embodiments, the pH-independent barrier coating system contains polyvinyl acetate polymer, which in certain embodiments in applied as an aqueous coating dispersion. The polyvinylacetate is insoluble in water at room temperature and may be used in either substantially pure form or as a blend. A commercial blend contains primarily a polyvinyl acetate polymer, a stabilizer, and minor amounts of a surfactant such as sodium lauryl sulfate. More specifically, a desirable aqueous based coating solution is KOLLICOAT® SR 30 D (BASF Corporation) and whose composition is about 27% polyvinyl acetate, about 2.7% polyvinylpyrrolidone (PVP), about 0.3% sodium lauryl sulfate (solids content 30% w/w). In one embodiment, if a substantially pure form of PVA is used, it can be dissolved in a suitable non-aqueous solvent to provide a coating solution for the drug ion-exchange resin complex. The KOLLICOAT® SR-30D aqueous dispersion may be cured for about 1 to about 24 hours. In alternate embodiments, the coating is cured for about 4 to about 16 hours, and preferably about 5 hours at high temperature, e.g., about 50° C. to about 65° C., and preferably about 60° C. Where the barrier coating comprises polyvinyl acetate, the polyvinyl acetate is present in an amount of about 70% to about 90% w/w of the final barrier coating layer, at least about 75%, at least about 80%, about 85% w/w of the final barrier coating layer. Where the barrier coating also comprises PVP as a stabilizer component (e.g., as is present in KOLLICOAT® ™ SR30D), the final barrier coating layer generally contains about 5 to about 10% w/w of polyvinyl pyrrolidone.

The granules further contain one or more gas generating agents. Gas generating agent generates nontoxic gas upon contact with gastric fluid and is selected from non-limiting list: comprising carbonates or bicarbonates of an alkali or alkaline earth metal such as potassium carbonate or potassium bicarbonate, sodium carbonate or sodium bicarbonate, calcium carbonate, sodium glycine carbonate, magnesium carbonate, and aluminum carbonate; and sulfites such as sodium sulfite, sodium bisulfite, and sodium metabisulfite. These salts may be used alone or in combination with an acid source as a gas-generating couple.

Granules further comprise one or more bulking agent selected from non-limiting list: microcrystalline cellulose, silicified MCC, dicalcium phosphate dehydrate.

Osmosis as Trigger

In certain embodiments, a composition of the invention contains at least one GHB drug; (i) at least one gelling agent as defined herein; (ii) at least one osmogent from the non-limiting list of osmogents; (iii) at least one water permeable diffusion barrier coating; (iv) an optional gas generating agent; and (v) optionally, a bulking agent.

Granules comprising at least one GHB drug(s) (e.g., at least a drug-ion exchange resin complex), gelling agent and osmogent are coated with the diffusion barrier. Without being bound by any theory, it is believed that upon coming into contact with aqueous medium; the osmogent promotes rapid water uptake. Gelling agent starts forming hydrogel and swelling and starts pushing the coat. Relative proportions of core excipients and coat thickness are optimized such that coat is removed completely due to swelling after 2 and before 6 hrs. Onset of second pulse is tailored by modifying the relative proportions of osmogent and gelling agent and; by modifying the coat thickness. Higher proportion of swelling enhancer and lower portion of gelling agent ensures rapid drug release once coat is removed.

Osmogent promotes rapid absorption of large amount of aqueous fluid. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide; xanthan gum; hydroxypropylmethyl cellulose; or mixtures thereof.

Optionally, the granules further comprise of one or more bulking agents, alternatively termed "fillers", such as are described throughout the specification.

In the following illustrative embodiments, the components are provided in percentages reflecting w/w of the trigger system.

pH as Trigger: Sigmoidal Release System:

This pulse trigger system comprises at least one GHB drug(s) and optionally at least one further biologically active moiety (e.g, an API, drug-ion exchange resin complex, or mixture thereof) plus: (i) a reverse enteric coated organic acid; (ii) an optional gas generating agent; (iii) optionally a bulking agent; (iii) at least one pH-independent, water-insoluble, water-permeable diffusion barrier coating polymer, e.g., ammonio Methacrylate Copolymer, Type A (e.g., Eudragit RL), and Ammonio Methacrylate Copolymer, Type B (e.g., Eudragit RS)). In certain embodiments, this pulse trigger system comprises at least one biologically active moiety in the form of drug-ion exchange resin complex, (about 60%, 10% w/w to 80% w/w of this pulse trigger system) plus: (i) a reverse enteric coated organic acid; (about 8%, 3% w/w to 25% w/w) (ii) an optional gas generating agent (about 5% w/w, 0 to 10% w/w); (iii) optionally a bulking agent (about 5%, 0 to 30% w/w); (iii) at least one pH-independent, water-insoluble, water-permeable diffusion barrier coating polymer, e.g., Ammonio Methacrylate Copolymer, Type B, (about 20%, 10% w/w to 60% w/w). Typically, an organic acid, after granulating with a diluent, is coated with reverse enteric polymer (e.g., Eudragit® EPO). These granules are further mixed with API (and optionally with gas generating agent and bulking agent) and granulated. These granules are coated with a pH-independent water insoluble water permeable diffusion barrier coating polymer, (e.g., /RL or blend). Without being bound by theory, it is believed that upon coming into contact with Gastric fluid, acidic medium entered into coated particles affects microenvironment pH. This increases permeability of reverse enteric coat on organic acid granules allowing release of organic acid. Based on pKa of organic acid and based on microenvironment pH, organic acid gets dissociated. Dissociated acid reacts with Ammonio Methacrylate Copolymer, Type A, Ammonio Methacrylate Copolymer, Type B or both (Eudragit RS/RL/both) present in the barrier coat and increases permeability of the coat resulting sigmoidal drug release generating the second pulse.

One or more organic acids are selected from non-limiting list: succinic acid, malic acid, fumaric acid, citric acid, tartaric acid and the likes and mixtures thereof.

A reverse enteric coating is pH-dependent and designed not to solubilize or swell in pH greater than about pH 4, or greater than about 4.5. One suitable reverse enteric polymer is an acrylate polymer or copolymer. Particularly suitable reverse enteric coats include those polymers which can be applied as aqueous dispersions. One suitable aqueous dispersion is based on methyl methacrylate and diethylaminoethyl methacrylate copolymer. One example of such a reverse enteric coat is Kollicoat® ® Smartseal 30D, which is an aqueous polymeric dispersion with a solids concentration of approximately 30%. It contains methyl methacrylate and diethylaminoethyl methacrylate copolymer stabilized with approximately 0.6% macrogol cetostearyl ether and 0.8% sodium lauryl sulfate. Still other reverse enteric polymers include, e.g., Eudragit® E 100 (Evonik), Eudragit® EPO (Evonik), methyl methacrylate, hydroxyl ethyl methacrylate and a random terpolymer based on methyl methacrylate, 2-hydroxy ethyl methacrylate and 4-vinylpyridine. The EUDRAGIT® EPO is Poly(butyl methacrylate-co-(2- dimethylaminoethyl) methacrylate-co-methyl methacrylate) 1:2:1 (CAS number: 24938-16-7), i.e., a cationic copolymer based on dimethylaminoethyl methacrylate, butyl methacrylate and methyl methacrylate. The commercial Eudragit® EPO Ready Mix consists of basic butylated methacrylate copolymer, sodium lauryl sulphate, stearic acid and talc. However, other surfactants, including other anionic surfactants, may be substituted for sodium lauryl sulfate in other formulations. Examples of suitable surfactants other than the anionic surfactant sodium lauryl sulfate are known to the skilled artisan. Similarly, lubricants other than stearic acid and glidants other than talc are known in the art and may be selected. Still other reverse enteric polymers are described, and may be made, as described, e.g., US 2006/062844 (2006); US 2005/0136114, U.S. Pat. No. 7,294,347, the disclosure of which is incorporated herein by reference. Weight percentages of these coatings, when present, are provided as weight added, in an amount of about 5% to about 60%, or about 5% to about 20%, or about 8 to about 12% weight added. In certain embodiments, the at least one reverse enteric polymer is selected from Eudragit EPO, Kollicoat® Smartseal 30 D, and uses thereof.

At least one pH-independent, water-insoluble, water-permeable diffusion barrier coating polymer (e.g., Eudragit RS) such as is defined herein covering the granules comprising the GHB drug(s), coated acid, optionally bulking agent and gas generating agent.

Optionally, the granules further comprise of one or more bulking agent.

Erosion as Trigger

In certain embodiments, a composition of the invention incudes at least one trigger erosion system. This system comprises: (i) at least one GHB drug(s) and optionally at least one further biologically active moiety (e.g, an API, drug-ion exchange resin complex, or mixture thereof)); (ii) at least one erosion barrier forming polymer selected from non-limiting list: HPMC, HEC, other cellulose ethers, guar gum; (iii) an optional gas generating agent; (iv) optionally, bulking agent. Suitably, the drug(s) and excipients are coated with the erodible barrier. In certain embodiments, the erosion trigger system comprises (i) at least one biologically active moiety (e.g., an API, drug-ion exchange resin complex, or mixture thereof) (about 60% w/w, 5% w/w to 80%/w/w); (ii) at least one erosion barrier forming polymer selected from non-limiting list: HPMC, HEC, other cellulose ethers, guar gum; (about 15%, 5% w/w to 20% w/w) (iii) an optional gas generating agent (about 7%, 0 to 15% w/w); (iv) optionally, bulking agent (about 15% w/w, 0 to 75% w/w). Suitably, the active moiety and excipients are coated with the erodible barrier.

Without being bound by theory, it is believed that upon coming into contact with aqueous medium; the coat starts eroding. The rate of coat erosion can be tailored by adjusting polymer solubility, viscosity, film thickness. The rate of coat erosion can be tailored by using polymer/s having different solubilities and dissolution rates, for example when working with cellulose ethers, those with small chain length (like ethyl, Hydroxy ethyl cellulose HEC) substitution have greater solubility and faster dissolution rate compared to those with longer chain length substitution (like hydroxyl propyl cellulose). The viscosity of coating polymer plays important role in tailoring coat erosion rate. Greater viscous polymer like HPMC K100M exhibits slower erosion rate compared to low viscosity polymers like HPMC K100LV. Greater coating level, slower is erosion. Thus, for slowing down erosion rate, slowly dissolving (e.g. HPC, HPMC), viscous polymer (viscosity >4000 cps) with higher coating levels (>20% w/w) are selected.

pH Plus Swelling as Trigger

In certain embodiments, a composition of the invention includes granules containing, at a minimum: (i) at least one GHB drug(s) and optionally at least one further biologically active moiety (e.g, an API, drug-ion exchange resin complex, or mixture thereof) (ii) at least one pH modifier; (iii) optionally a swelling agent. The granule is coated with at least one enteric polymer and the coated granules are further coated optionally with a reverse enteric polymer. In certain embodiments, a composition of the invention includes granules containing, at a minimum: (i) at least one GHB drug(s) and optionally at least one further biologically active moiety (e.g, an API, drug-ion exchange resin complex, or mixture thereof), (about 40%, 10% w/w to 75% w/w) (ii) at least one pH modifier (about 20%, 5% w/w to 50% w/w); (iii) optionally a swelling agent (about 10% w/w, 5% w/w to-25% w/w). The granules are coated with at least one enteric polymer and the coated granules are further coated optionally with a reverse enteric polymer.

Without being bound by theory, it is believed that alkaline microenvironment pH created by pH modifier results in dissolution of enteric polymer. Swelling further results in eruption of outer coat which also dissolves in surrounding acidic pH. Various approaches may be used to modify the onset of the second trigger pulse between 2 to 6 hours, including, e.g., the level of enteric coat, the level of level of reverse enteric coat, the swelling agent, and pH modifier enables one to tailor the time for second pulse of API release.

A variety of enteric coatings are known and/or commercially available. Such enteric coatings are pH-dependent, being designed to be stable at pH of about 1 to about 3.5 to about 4 which is present in stomach acid to dissolve in the higher small intestine (e.g., about 7 to about 9). Certain pH-dependent (enteric) polymers including, e.g., members of the EUDRAGIT polymer family, e.g., the L, S, and E, polymers and others which are commercially available may be selected.

Compositions as provided herein may contain a combination of a first pulse release system, one or more of the preceding trigger pulse release systems and/or a combination of a first pulse release and one or more of these trigger pulse systems with yet another pulse release system. Such pulse release systems are incorporated into compositions as provided herein with other suitable components.

Components of Gastro-Retentive Raft Pulse Release

In addition to the at least two pulse GHB drug release systems in the compositions of the invention, the compositions further contain, among other components, one or more gastro-retentive raft forming systems. Such raft forming systems are designed to form in vivo (in situ) in the presence of gas and to entrap one or more pulses, at least one of which is a trigger pulse system. Optionally, the first (or immediate release) pulse is provided by the composition but is not entrapped within the raft. A variety of raft forming systems may be selected.

Ionic Cross-Linking Based Raft Forming System

In certain embodiments, an ionic cross-linking based raft forming system is selected. This system comprises: at least one anionic polymer in an amount of about 2% w/w to about 75% w/w, or about 2% w/w to about 50% w/w, or about 5% w/w to about 40% w/w, or about 10% w/w to about 30% w/w, or about 10% w/w to about 75% w/w, or about 15% w/w to about 65% w/w, or about 20% w/w to about 55% w/w, or about 25% w/w to about 45% w/w, of the raft forming system. One or more anionic polymer(s) may be selected from the following non-limiting list: sodium alginate, carrageenan I, pectin, gellan gum, alginic acid, carrageenan k, sodium carboxy methyl cellulose, and/or xanthan gum; at least one cross-linking agent selected from the following non-limiting list of divalent and trivalent metal salts: Calcium salts like calcium carbonate, calcium chloride, calcium gluconate; magnesium salts, ferrous salts, ferric salts, aluminum salts, and/or zinc salts; at least one gas generating agent like sodium bicarbonate, ammonium bicarbonate, calcium carbonate, sodium carbonate which generates carbon dioxide gas upon reacting with acid and/or a sulfite; and optionally, an effervescent couple.

Without wishing to be bound by theory, it is believed that upon coming into contact with acidic medium, the anionic polymer gets crosslinked with cross linking agent. Gas (e.g., carbon dioxide) generated by a gas generating agent after reacting with stomach acid gets entrapped in the cross-linked polymer causing latter to float. Optionally, an effervescent couple is used to liberate carbon dioxide gas.

A variety of anionic polymers may be selected including, e.g., one or more: pectins, alginic acid, gellan gum, carrageenan, and xantham gum, and/or combinations thereof. Pectins are a family of polysaccharides in which the polymer backbone mainly comprises α-(1-4)-D galacturonic acid residues. Free calcium ions crosslink the galacturonic acid chains and may be included in the formulation for induction of pectin cross-linking. Advantageously, pectin is water soluble, so organic solvents are not necessary in the formulation. Alginic acid is a linear block copolymer polysaccharide consisting of β-D-mannuronic acid and α-L-glucuronic acid residues joined by 1,4-glycosidic linkages. Aqueous solutions of alginates undergo crosslinking with di- and trivalent metal ions by a cooperative process involving consecutive glucuronic residues in the α-L-glucuronic acid blocks of the alginate chain. Gellan gum (commercially available as Gelrite™ or Kelcogel™) is an anionic deacetylated exocellular polysaccharide with a tetrasaccharide repeating unit of one α-L-rhamnose, one β-D-glucuronic acid and two β-D-glucuronic acid residues. Carrageenans are a family of linear sulfated polysaccharides. There are three main varieties of carrageenan, which differ in their degree of sulphation. Kappa-carrageenan has one sulphate group per disaccharide, Iota-carrageenan has two, and Lambda-carrageenan has three. Iota carrageenan is cross linked by divalent cations while kappa carrageenan is cross-linked by monovalent cations. Xanthan gum is anionic polysaccharide composed of pentasaccharide repeat units, comprising glucose, mannose, and glucuronic acid in the molar ratio 2:2:1.

Swelling Based Raft Forming System

In certain embodiments, a composition as provided herein comprises a swelling based raft forming system. This system comprises: (i) at least one swelling agent selected from non-limiting list: pH dependent swelling agent (e.g., like poly (acrylic acid) (PAA) (e.g., Carbopol® 971P), other carbomers, chitosan), pH independent swelling agent (e.g., like polyox, HPMC, other cellulose ether)s; (ii) optionally, at least one gas generating agent; (iii) optionally one or more pH modifiers; (iv) an optional effervescent couple. For example, one swelling raft system comprises: (i) at least one swelling agent (about 30%, 10% w/w to 75% w/w of the raft); (ii) at least one gas generating agent; potassium bicarbonate (about 10%, 5% w/w to about 30% w/w) (iii) optionally one or more pH modifiers; sodium bicarbonate (about 10% w/w, 5 w/w to about 30% w/w). For example, another swelling raft system comprises: (i) at least one swelling agent (about 30% w/w, 10% w/w to about 75% w/w of the raft)(e.g., about 30% Polyox); (ii) at least one gas generating agent (5% w/w to 30% w/w, or about 10%, (e.g, potassium bicarbonate).

Various pH dependent polymers may be used which cause the formation of in situ gel in the system. Various polymers such as PAA (Carbopol®, carbomer) or its derivatives, polyvinylacetal diethylaminoacetate (AEA), mixtures of poly(methacrylic acid) (PMA) and poly(ethylene glycol) (PEG) show change from sol to gel with change of pH. Swelling of hydrogel increases as the external pH increases in the case of weakly acidic (anionic) groups, but decreases if polymer contains weakly basic (cationic) groups. Mixtures of poly(methacrylic acid) (PMA) and poly(ethylene glycol) (PEG) also have been used as a pH sensitive system to achieve gelation. pH sensitive polymer can be neutral or ionic in nature. The anionic networks contain negatively charged moieties, cationic networks contain positively charged moieties, and neutral networks contain both positive and negatively charged moieties. In the case of anionic polymeric network containing carboxylic or sulphonic acid groups, ionization takes place, as the pH of the external swelling medium rises above the pKa of that ionizable moiety.

Carbopol is a mucoadhesive polymer that increases the formulation's mechanical strength, but also increases surface interaction with the ocular tissue and consequently contact time. Carbopol shows a solid-to-gel transition in aqueous solution as the pH is raised above its pKa of about 5.5; therefore, to have an easy administration, an acidic pH would be needed before carbopol phase transition. Chitosan is a cationic polysaccharide consisting copolymers of glucosamine and N-acetyl glucosamine, these are natural polymer obtained by deacetylation of chitin. It is nontoxic, biocompatible, biodegradable polysaccharide and having bioadhesive, antibacterial activity. Chitosan aqueous solution forms a hydrated gel, like precipitate, at pH exceeding 6.2.

Temperature Dependent Gelling Based Raft Forming System

In certain embodiments, the composition comprises a temperature dependent gelling raft forming system. Such a system may comprise (i) optionally at least one gelling agent which gels at 37° C., but which remains dissolved at room temperature (e.g., about 25% w/w to about 80% w/w, 30% w/w to about 75% w/w, or about 40% w/w to about 65% w/w, or about 45% w/w to about 55% w/w, of the raft forming system). Examples of suitable gelling agents may be selected from the following non-limiting list: Xyloglucan, poloxamer 188, Poloxamer 407, and combinations thereof. The system further contains (ii) at least one gas generating agent (e.g., about 10% w/w to about 40% w/w, or about 15% w/w to about 35% w/w, or about 20% w/w to about 30% w/w of the raft forming system) and, additionally, an optional effervescent couple. For example, one temperature dependent gelling based raft forming system comprises poloxamer 407 (about 50%, 25% w/w to 80% w/w of the raft forming system, sodium bicarbonate (about 25%, 10% w/w to 40% w/w). In another example, temperature dependent gelling based raft forming system comprises poloxamer 188 (40%, 205-80% w/w of the raft forming system, sodium bicarbonate (about 25%, 10% w/w to-40% w/w) of the raft forming system.

Xyloglucan is a polysaccharide composed of a (1-4)-β-D glucan backbone chain, which has (1-6)-α-D xylose branches that are partially substituted by (1-2)-β D galactoxylose. When xyloglucan is partially degraded by β-galactosidase, the resultant product exhibits thermally reversible gelation by the lateral stacking of the rod like chains. The sol-gel transition temperature varies with the ° of galactose elimination. It forms thermally reversible gels on warming to body temperature. Its potential application in oral delivery exploits the proposed slow gelation time (several minutes) that would allow in situ gelation in the stomach following the oral administration of chilled xyloglucan solution.

Cross-Linked Galactomannan Based Raft Forming System

In certain embodiments, the composition comprises at least one cross-linked galactomannan based raft forming system. This system typically comprises: (i) at least one galactomannan polysaccharide in an amount of about 30% w/w to about 80% w/w, or about 30% w/w to about 60% w/w, or about 35% w/w to about 55% w/w of the raft forming system which may be selected from the following non-limiting list: guar gum, fenugreek gum, locust bean gum; (ii) at least one cross-linking agent in an amount of about 5% w/w to about 20% w/w, or about 5% w/w to about 15% w/w, or about 10% w/w of the raft forming system which may be selected from the following non-limiting list: borax, glutaraldehyde, divalent metal salts, trivalent metal salts; (iii) optionally at least one gas generating agent in an amount of about 2% w/w to about 20% w/w, or about 2% w/w to about 15% w/w, or about 2% w/w to about 10% w/w, or about 5% w/w to about 20% w/w, or about 10% w/w to about 20% w/w; and (iv) optionally, a pH modifier may be added to promote the galactomannan cross-linking. In certain embodiments, crosslinked galactomannan based raft forming system comprises, guar gum (about 50% w/w, 30% w/w to 80% w/w), borax (about 10%, 6% w/w to 16% w/w), dibasic calcium phosphate dehydrate (about 5%, 2% w/w to 20% w/w). In certain embodiments, crosslinked galactomannan based raft forming system comprises fenugreek gum (about 50%, 30% w/w to 80% w/w), borax (about 10%, 6% w/w to 16% w/w), meglumine (about 5%, 2% w/w to 20% w/w).

Galactomannans are polysaccharides consisting of a mannose backbone with galactose side groups (more specifically, a (1-4)-linked beta-D-mannopyranose backbone with branch-points from their 6-positions linked to alpha-D-galactose, i.e. 1-6-linked alpha-D-galactopyranose). Examples of suitable galactomannans include, in order of increasing number of mannose-to-galactose ratio: fenugreek gum, mannose:galactose ~1:1; guar gum, mannose:galactose ~2:1; tara gum, mannose:galactose ~3:1; locust bean gum or carob gum, mannose:galactose ~4:1. These are not limitations on the galactomannans which are useful and which may be obtained from a variety of sources, including those identified below.

Galactomannans of Leguminosae Species

| Botanical name | | |
|---|---|---|
| Subfamily | Species | M/G ratio |
| CAESALPINIACAE | Cassia absus | 3.00 |
| | C. emarginata | 2.70 |
| | C. Fistula | 3.00 |
| | C. leptocarpa | 3.05 |
| | C. marylandica | 3.76 |
| | C. nodosa | 2.7-3.5 |
| | C. occidentalis | 3.00 |
| | C. tora | 3.00 |
| | Ceratonia siliqua | 3.75 |

-continued

| Botanical name | | |
|---|---|---|
| Subfamily | Species | M/G ratio |
| | Caesalpinia cacalaco | 2.50 |
| | C. pulcherima | 2.7 |
| | C. spinosa | — |
| | Cercidium torreyanum | 3.38 |
| | Delonix regia | 4.28 |
| | Gleditsia amorphoides | 2.5 |
| | G. triacanthos | 3.2 |
| | Gymnocladus dioica | 2.71 |
| | Parkinsonia aculeata | 2.70 |
| MIMOSACEAE | Besmanthus illinoensis | 2.69 |
| | Leucaena galauca | 1.33 |
| FABACEAE | Sophora japonica | 5.19 |
| | Genista raetam | 4.14 |
| | G. scoparia | 1.59 |
| | G. cretica | 1.58-167 |
| | G. foenum-graecum | 1.2 |
| | G. hamosa | 1.17 |
| | G. monspeliaca | 1.08 |
| | G. polyserata | 1.13 |
| | G. radiata | 1.17 |
| | Anythyllis vulneraria | 1.33 |
| | Lotus corniculatus | 1.25 |
| | L. pedunculatus | 1.04 |
| | L. scoparius | 1.13 |
| | Alysicarpus veginalis | 1.14 |
| | Desmodium pulchellum | 2.00 |

TABLE 2

Galactomannans of non-leguminous plants

| Botanical name | | M/G ratio |
|---|---|---|
| ANNONACEAE | Annona muricata | 4.46 |
| CONVOLVULACEAE | Convolvulus tricolor | 1.75 |
| | Ipomoea muricata | 1.8 |
| EBENACEAE | Diospyros virginiana | — |
| LOGANIACEAE | Strychnos nux-vornica | — |
| PALMAE | Borassus flabellifer | 2.4 |
| | Cocos mucifera | 2.57 |
| | Arenga saccharifera | 2.26 |
| | Phytelephas macrocarpa | 50 |
| | Hyphaene thebaica | 19 |
| | Phoenix dactylifera | 10 |

Suitable cross-linking agent for use with a galactomannan may selected from the following non-limiting list: borax, glutaraldehyde, boric acid, organotitanates, other organometallic crosslinkers including Zr, Al, Cr, or combinations thereof Liquid Crystal Based Raft Forming System.

In certain embodiments, the composition comprises at least one liquid crystal based raft forming system. Such a system typically comprises: (i) at least one liquid crystal forming substance in an amount of about 30% w/w to about 80% w/w, or about 35% w/w to about 70% w/w, or about 40% w/w to about 60% w/w or about 50% w/w of the raft forming system, (ii) at least one gas generating agent in an amount of about 10% w/w to about 25% w/w, or about 15% w/w to about 25% w/w, or about 10% w/w to about 20% w/w, or about 15% w/w) and iii) optionally a diluent. An example of a liquid crystal forming substance includes glyceryl monooleate (GMO, 2,3-dihydroxypropyl oleate). Other suitable liquid crystal forming substances may include, e.g., phytantriol (PT, 3,7,11,15-tetramethyl-1,2,3-hexadecanetriol) and other lipids such as monolinolein, monoelaidin, phosphatidylethanolamine, oleoylethanolamide, phospholipids, PEGylated phospholipids, D-α-polyethylene glycol, alkyl glycerates, and glycolipids; Oleyl glycerate (OG,2,3-dihydroxypropionic acid octadec-9-enyl ester) and phytanyl glycerate (PG, 2,3-dihydroxypropionic acid 3,7,11,15-tetramethyl-hexadecyl ester). In certain embodiments, liquid crystal based raft forming system comprises D-α-polyethylene glycol (TPGS) (about 50% w/w, 30% w/w to about 80% w/w of the raft forming system), sodium bicarbonate (about 15%, 10% w/w to 25% w/w). In certain embodiments, liquid crystal based raft forming system comprises GMO (about 50% w/w, 30% w/w to 80% w/w), sodium bicarbonate (about 15% w/w, 10% w/w to 25% w/w), microcrystalline cellulose (MCC) (about 15%, 10% w/w to about 25% w/w).

In certain embodiments, a composition of the invention may include more than one Raft forming system.

GHB Compositions

The compositions provided herein may be useful for delivering at least one GHB drug(s) and at least one optional, additional biologically active moiety, each of which may be one or more forms, such as in "free form" or as particles, granules, or drug-ion exchange resins complexes, etc, as described in this specification. Regardless of the form in which they are to be incorporated in the compositions, the selected biologically useful moieties or their particles, granules, complexes, etc, selected for inclusion in the composition have an average size of less than about 500 microns in size, preferably less than about 425 microns. However, moieties (particles, granules, complexes, etc) having a larger size may be selected depending upon the total weight (dose) being delivered and/or by adjusting the amount of gas generating agent.

One or more drugs may be used in at least one drug-ion exchange resin complex. Typically, this involves exchanging the salt of the compound (e.g., a drug or mineral) with the counterion from an ion exchange resin. In certain embodiments, two or more drug-ion exchange resin complexes having different drugs may be used in a single composition. In certain embodiments, two or more drug-ion exchange resin complexes which are in different release forms, e.g., immediate release, modified release, including different modified release coatings, may be used in a single composition.

Methods of complexing drugs with ion exchange resins is known in the art. For example, suitable methods for preparing such complexes and examples of suitable ion exchange resins are described in U.S. Pat. Nos. 8,062,667, 8,287,848, 8,202,542, which are incorporated herein by reference. Ion exchange resins suitable for pharmaceutical use are typically water-insoluble and comprise a preferably pharmacologically inert organic and/or inorganic matrix containing functional groups that are ionic or capable of being ionized under the appropriate conditions of pH, in order to permit ion exchange with the drug (other moiety) being complexed therewith. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are suitable for use in the controlled release of drug preparations. Such ion-exchangers are described by H. F. Walton in "Principles of Ion Exchange" (pp: 312-343) and "Techniques and Applications of Ion-Exchange Chromatography" (pp: 344-361) in Chromatography. (E. Heftmann, editor), van Nostrand Reinhold Company, New York (1975). Ion exchange resins that can be used in the present invention have exchange capacities of about 6 milliequivalents (meq)/gram and preferably about 5.5 meq/gram or below. Typically the size of the ion-exchange particles is from about 5 microns to about 750 microns, preferably the particle size is within the range of about 40 microns to about 250 microns for liquid dosage forms although particles up to about 1,000 micron can be used for solid dosage forms, e.g., tablets, pellets, powders (including powders for suspensions), and capsules. Particle sizes substantially below the lower limit are generally difficult to handle in all steps of the processing. Generally, uncoated drug-ion exchange resin particles will tend to be at the lower end of this range, whereas coated drug-ion exchange resin particles will tend to be at the higher end of this range. However, both uncoated and coated drug-ion exchange resin particles may be designed within this size range.

Ion exchange resins are broadly classified into two main categories, as cation exchange resins and anion exchange resins. GHB (e.g., oxybate salts), exchange counterions with and bind to an anion exchange resin. Anion exchange resins can be prepared by first chloromethylating the benzene rings of styrene-divinylbenzene copolymer to attach $CH_2Cl$ groups and then causing these to react with tertiary amines such as triethylamine. A strong base type anion exchange resin is highly ionized and exchange capacity is not affected by pH. In certain embodiments, a strongly basic anion exchanger contains quaternary ammonium groups attached to a styrene and divinylbenzene copolymer. Suitable pharmaceutical grade anion exchange resins may be obtained commercially. An example of strong base anion exchange resin is cholestyramine. See, e.g, Duolite AP143/1083 is cholestyramine USP supplied by Dow Chemical Company. A weak base type anion exchange resins exhibit minimal exchange capacity above pH 7. An example of a weakly basic anion exchangers contain polyalkylamine groups attached to a styrene and divinyl benzene.

Inorganic ion exchangers include zeolites, which are microporous, aluminosilicate minerals. Zeolites have a porous structure that can accommodate a wide variety of cations, such as Na+, K+, Ca2+, Mg2+ and others. These positive ions are rather loosely held and can readily be exchanged for others in a contact solution. Some of the more common mineral zeolites are analcime, chabazite, clinoptilolite, heulandite, natrolite, phillipsite, and stilbite. An example of the mineral formula of a zeolite is: $Na_2Al_2Si_3O_{10}.2H_2O$, the formula for natrolite.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin with a granulating agent and optional modified release coating.

Binding of the selected drug or combination of drugs to the ion exchange resin can be accomplished using methods known in the art. The binding may be performed, for example as a batch or column process, as is known in the art.

Typically the drug-ion exchange resin complex thus formed is collected by filtration and washed with appropriate solvents to remove any unbound drug or by-products. The complexes can be air-dried in trays, in a fluid bed dryer, or other suitable dryer, at room temperature or at elevated temperature.

In one example, drug-ion exchange resin complex can be prepared by dissolving the drug(s) in deionized water, adding ion exchange resin USP under stirring and continuing stirring further. The stirring is continued further for a period of 15 min to 20 hrs. More preferably, for 30 min to 10 hr, more preferably from 1 hr to 5 hr. In one embodiment, the drug-ion exchange resin complexes can be prepared using methods known in the art, such as, but not limited to, blending, slurrying, kneading, grinding, sieving, filling, compressing, lyophilization, spray-drying, fluid-bed drying or centrifugal granulation. The drug-resin binding may be performed, for example, as a batch or column process, as is known in the art. In one illustrative embodiment, drug-ion exchange resin complex is prepared by batch process. In one embodiment the drug-resin complexes were prepared by stirring aqueous slurry of drug and ion exchange resin for about 0.5 hours to about 12 hours, followed by filtration and drying of the formed drug-ion exchange resin complex. Drug: ion exchange resin by weight ratio in the complex (also termed a resinate) can be from 1:0.1 to 1:100, more preferably from 1:1 to 1:10. The amount of drug that can be loaded onto a resin will typically range from about 1% to about 75% by weight of the drug-ion exchange resin particles. In one embodiment, loading of about 10% to about 40% by weight, more desirably, about 15% to about 30% by weight, of the drug-ion exchange resin particles can be employed. Typical loadings of about 25% by weight of the drug-ion exchange resin particles can be advantageously employed.

Optionally, a drug-ion exchange resin complex may be granulated with a polymer in preparation for formulation and/or for further processing (e.g., coating). Such a polymer may optionally provide modified release properties to the drug(s) in the complex. Suitably, the granulating agent does not form a separate coating layer on the drug-ion exchange resin complex, but forms a matrix therewith. Examples of suitable polymer systems include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems. One suitable polymer system which may provide release retardant properties is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members of the EUDRAGIT polymer family, e.g., the L, S, and E, polymers may be selected. Examples of polymers and/or polymer systems which do not provide any significant release retardant properties include the impregnating agents described for example in U.S. Pat. No. 4,221,778 and published US Patent Application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON® K30) mannitol, methyl cellulose, hydroxypropyl methylcellulose, hydroxypropyl cellulose, and sorbitol.

The quantity of the granulating agent typically ranges from about 3% to about 30% or more by weight of the uncoated drug-ion exchange resin particles. More preferably the granulating agent, if used, is in the range from about 5% to about 20% and most preferably in the range of about 10% to about 15% by weight of the uncoated drug-ion exchange resin particles. These granulating agents can be added during the formation of the drug-ion exchange resin complex either in the beginning, during the middle, or after substantial amount of complex formation has taken place. In the more preferred embodiment, the retardant is added after the formation of drug-ion exchange resin complex. Upon admixing, the drug-ion exchange resin complex particles with the granulating agent, the mixture is dried and milled appropriately. In some cases, the milling may be carried out before the complete drying of the complex and then again further drying followed by milling to obtain the desired size or other desired characteristics.

Pharmaceutically Acceptable Excipients

The compositions of the invention may be, e.g., a powder, powder for suspension (POS), powder in capsule, or suspension. The excipients for the composition are selected accordingly. Excipients in a suspension and/or ER POS may include suspending agents and/or thickening agent, wetting agents, and/or preservatives. Excipients are discussed in subsequent section.

The timing, pulse release compositions provided herein are generally dosed in the form of suspensions from powders admixed with a suspension base, preferably an aqueous suspension base. As used herein, an aqueous suspension refers to a suspension in which at least about 50% v/v of the liquid component of the suspension is water, preferably greater than about 60% w/v, greater than about 80% w/w, at least about 90% up to 100%. The suspension base may further contain comprises binders, diluents, salivating agents, surfactants, flavors, sweeteners, colorants, souring agents, viscolizers, glidants, chelating agents, lubricants, solubilizers, stabilizers, suspending agents, preservatives, cosolvents, anti-caking agents, buffers and the like or any combinations thereof. Examples of suitable binders include, but are not limited to, starch, pregelatinized starch, polyvinyl pyrrolidone, copovidone, cellulose derivatives, such as hydroxypropylmethyl cellulose, hydroxypropyl cellulose and carboxymethyl cellulose and their salts. Examples of suitable diluents include, but are not limited to, starch, microcrystalline cellulose, lactose, xylitol, mannitol, maltose, polyols, fructose, guar gum, sorbitol, magnesium hydroxide, dicalcium phosphate, coprocessed mannitol and calcium silicate and the like or any combinations thereof. Examples of lubricants include, but are not limited to, magnesium stearate, calcium stearate, stearic acid, talc, and sodium stearyl fumarate. Suitable glidants includes but are not limited to, colloidal silica, silica gel, precipitated silica, or combinations thereof. Suitable salivating agents include, but are not limited to, micronised polyethylene glycol, sodium chloride or precipitated micronised silica. Examples of solubilizers include, but are not limited to cetostearyl alcohol, cholesterol, diethanolamine, ethyl oleate, ethylene glycol palmitostearate, glycerin, glyceryl monostearate, isopropyl myristate, lecithin, medium-chain glyceride, monoethanolamine, oleic acid, propylene glycol, polyoxyethylene alkyl ether, polyoxyethylene castor oil glycoside, polyoxyethylene sorbitan fatty acid ester, polyethylene sorbitan fatty acid ester, polyoxyethylene stearate, propylene glycol alginate, sorbitan fatty acid ester, stearic acid, sunflower oil, triethanolmine, or combinations thereof. Souring agents include, but are not limited to, monosodium fumarate and/or citric acid. The compositions of the present invention may also include stabilizers such as, but not limited to, those described above under drug-resin complexes. Suitable chelating agents that may be employed have been discussed herein above. Suitable viscolizers include, but are not limited to, coprocessed microcrystalline cellulose such as but not limited to, Avicel RC591, Avicel CL-611, D-sorbitol solution, polyalkylene oxides such as, but not limited to polyethylene oxide; cellulose ethers such as, but not limited to hydroxyethyl cellulose, hydroxypropylcellulose, hydroxypropyl methyl cellulose, methyl cellulose, ethyl cellulose, sodium carboxy methylcellulose, calcium carboxymethyl cellulose, microcrystalline cellulose; gums such as but not limited to gum arabic alginates, agar, sodium alginate guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan; polyols such as, but not limited to dipropylene glycol, polypropylene glycol, propylene glycol, polyethylene glycol (PEG), sorbitol and glycerol; carbopol, starch and starch-based polymers such as, but not limited to, pregelatinized starch, acrylic acid and methacrylic acid polymers, and esters thereof, maleic anhydride polymers; polymaleic acid; poly(acrylamides); poly(olefinic alcohol)s; poly(N-vinyl lactams); polyoxyethylated saccharides; polyoxazolines; polyvinylamines; polyvinylacetates; polyimines; povidone, vinylpyrrolidone/vinyl acetate copolymer and polyvinyl acetate, mixture of polyvinyl acetate and polyvinylpyrrolidone, chitin, cyclodextrin, gelatin, chitosan and the like or any mixtures thereof. Suitable surfactants include, but are not limited to, anionic, nonionic, cationic, and zwitterionic surfactants or a mixture thereof. The non-ionic surfactants employed in the composition may include, but are not limited to, ethoxylated fatty acid ester, ethoxylated fatty acid ethers, ethoxylated sorbitan ethers, ethoxylated alkyl-phenols, glycerol esters, glycerol sugar esters, polyoxyethyleneglycerol monolaurate, polyoxyethyleneglycerol monostearate, polyoxyethylene-20-cetyl stearate, polyoxyethylene-25-cetyl stearate, polyoxyethylene (25)-oxypropylene monostearate, polyoxyethylene-20-sorbitan monopalmitate, poly-oxyethylene-16-tert-octyl phenol, polyoxyethylene-20-cetyl ether, polyethylene glycol (1000) monocetyl ether, ethoxylated castor oil, polyoxyethylene sorbitol-lanolin derivatives, polyoxyethylene(25)propylene glycol stearate, polyoxyethylenesorbitol esters, polyoxyethylene-20-sorbitan monopalmitate, polyoxyethylene-16-tert-octylphenol, polyoxyethylene-20-cetyl ether, glycyeryl undecylenate and Polysorbate 60, capmul (medium chain glyceride), peceol (glyceryl monooleate), glyceryl laurate and glyceryl caprylate (Capmul MCM), PEG sorbitan fatty acid esters like PEG-20 sorbitan monolaurate (Tween 20), PEG-20 sorbitan monostearate (Tween 60), PEG-20 sorbitan monooleate (Tween 80), sorbitan fatty acid esters like sorbitan monolaurate (Span 20), glyceryl stearate (Cithrol GMS) or the like and mixtures thereof. Suitable cationic surfactants include, but are not limited to, quaternary ammonium compounds, alkylamidoamines and quaternary ester compounds, distearyl dimethyl ammonium chloride, dimyristyl dimethyl ammonium chloride, dipalmityl dimethyl ammonium chloride or the like and mixtures thereof. Suitable anionic surfactants include, but are not limited to, fatty alcohol sulfates, alpha olefin sulfonates, sulfosuccinates, phosphate esters, carboxylates, sarcosinates, alkyl benzene sulfonates, alkyl sulfonates, olefin sulfonates, alkyl ethersulfonates, glycerol ethersulfonates, a-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates, alkyl (ether)phosphates or the like and mixtures thereof. Suitable zwitterionic surfactants employed include, but are not limited to, N-alkyl-N,N-dimethyl ammonium glycinates, for example cocoalkyl dimethyl ammonium glycinate, N-acyl aminopropyl-N,N-dimethyl ammonium glycinates, cocoacyl aminoethyl hydroxyethyl carboxymethyl glycinate or the like and mixtures thereof. Further, the composition of the present invention may further comprise a preservative such as but not limited to methyl parahydroxybenzoate, propyl parahydroxybenzoate and sodium benzoate. Suitable cosolvent that may be used includes, but is not limited to, ethanol and polyhydric alcohols such as, but not limited to, glycerin, propylene glycol, low molecular weight polyethylene glycols, and mixtures thereof. Further anti-caking agents that may be optionally incorporated include, but are not limited to, colloidal silicon dioxide, tribasic calcium phosphate, powdered cellulose, magnesium trisilicate, starch, and mixtures thereof. Suitable sweetening agent includes, but is not limited to, aspartame, *stevia* extract, *glycyrrhiza*, saccharine, saccharine sodium, acesulfame, sucralose, dipotassium glycyrrhizinate, galactose, fructose, high fructose corn syrup, dextrose, sucrose, sugar, maltose, partially hydrolyzed starch, corn syrup solids, sorbitol, xylitol, mannitol and the like or mixtures thereof. The compositions may comprise one or more natural and/or artificial flavors such as, but not limited to, mint flavour, orange flavour, lemon flavors, strawberry aroma, vanilla flavour, raspberry aroma, cherry flavor, tutti frutti flavor, magnasweet 135, key lime flavor, grape flavor, trusil art 511815, and fruit extracts and the like. Suitable colorants include, but are not limited to, pigments and dyes such as FD&C Red, FD&C Yellow, FD&C Green, and FD&C Blue and the like or combinations thereof.

The GHB composition which forms a gastro-retentive RAFT having at least two trigger pulses, the composition comprise: (a) at least one GHB drug(s) in an immediate release pulse release form; (b) at least one GHB drug(s) in a delayed trigger release form; and (c) a RAFT system, wherein following oral ingestion, the composition provides a self-assembling gastro-retentive RAFT having entrapped therein, the at least one drug of (a) and (b) and the gas generated in situ by the non-toxic gas generating agent, thereby providing a floating gastro-retentive RAFT having a dual pulse system wherein at least the second pulse is a trigger pulse and which retains the at least one drug in the stomach for at least about 3 hours. Optionally, the composition may contain one or more additional drug(s) in combination with the GHB drug(s), optionally in a first, second, or subsequent pulse.

In certain embodiments, the GHB composition comprises a pH sigmoidal delayed trigger system which comprises particles comprising: (a) at least one GHB drug(s) (e.g., a GHB drug-ion exchange resin complex) and at least one optional biologically active moiety; an organic acid coated with a reverse enteric coat; an optional gas generating agent; an optional bulking agent; and (b) Ammonio Methacrylate Copolymer, Type A (e.g., Eudragit RL), or Ammonio Methacrylate Copolymer, Type B (e.g., Eudragit RS) or both coat over the particles of (a), wherein said coat dissolves in the presence of the organic acid of (a), whereby following ingestion in the presence of acid a RAFT comprising a pH sigmoidal delayed trigger for the drug of (a) is formed. In certain embodiments, this pulse trigger system comprises at least one GHB drug(s) and/or at least one optional biologically active moiety in the form of drug-ion exchange resin complex (about 60% w/w, 10% w/w to 80% w/w of this pulse trigger system) plus: (i) a reverse enteric coated organic acid; (about 8%, 3 to 25% w/w) (ii) an optional gas generating agent (about 5%, 0 to 10% w/w); (iii) optionally a bulking agent (about 5%, 0 to 30% w/w); (iv) at least one pH-independent, water-insoluble, water-permeable diffusion barrier coating polymer, e.g., Ammonio Methacrylate Copolymer, Type B, (about 20%, 10 to 60% w/w) based on the weight of the trigger system. The compos In certain embodiments, this pulse trigger system comprises at least one GHB drug and at least one optional biologically active moiety about 10%, 5% w/w to 40% w/w of trigger system) plus (i) a reverse enteric coated organic acid; (about 3% w/w, 1 w/w to 10% w/w)) (ii) an optional gas generating agent (about 2%, 0 to 6% w/w) (iii) optionally a bulking agent (about 10%, 5% w/w to 25% w/w)) (iv) at least one pH-independent, water-insoluble, water-permeable diffusion barrier coating polymer, (e.g., Ammonio Methacrylate Copolymer, Type B), about 10%, 4% w/w to 40% w/w, of the trigger system.

In certain embodiments, the GHB composition comprises an erosion delayed trigger system which comprises: at least one erosion barrier forming polymer; an optional gas generating agent; at least one GHB drug(s) (e.g., a GHB drug-ion exchange resin complex) and at least one optional biologically active moiety; and an optional bulking agent, whereby in the presence of stomach acid, a RAFT comprising the erosion delayed trigger system for the drug is formed. In certain embodiments, the erosion trigger system comprises (i) at least one GHB drug(s) (e.g., a GHB drug-ion exchange resin complex) and at least one optional biologically active moiety; (about 60%, 5% w/-80% w/w) (ii) at least one erosion barrier forming polymer selected from non-limiting list: HPMC, HEC, other cellulose ethers, guar gum; (about 15%, 5% w/w to 20% w/w) (iii) an optional gas generating agent (about 7% w/s, 0 to 15% w/w); (iv) optionally, bulking agent (about 15% w/w, 0 to 75% w/w) of the trigger system. Suitably, the active moiety and excipients are coated with the erodible barrier In certain embodiments, the GHB composition has a pH, swelling delayed trigger system, comprising: (i) granules comprising at least o at least one GHB drug(s) (e.g., a GHB drug-ion exchange resin complex) and at least one optional biologically active moiety, at least one pH modifier, at least one swelling agent, optionally a gas generating agent are coated with at least one enteric polymer, (ii) Reverse enteric coat over the granules of (i), whereby in the presence of stomach acid, a RAFT comprising the pH-swelling delayed trigger system for the drug of (i) is formed. In certain embodiments, a composition of the invention includes granules containing, at a minimum: (i) at least one GHB drug(s) and an optional biologically active moiety (e.g., a drug, drug-ion exchange resin complex, or mixture thereof), (about 40% w/w, 10% w/w to-75% w/w) (ii) at least one pH modifier (about 20% w/w, 5% w/w to 50% w/w); (iii) optionally a swelling agent (about 10% w/w, 5% w/w to 25% w/w) of the trigger system. The granules are coated with at least one enteric polymer and the coated granules are further coated with a reverse enteric polymer.

In certain embodiments, the GHB composition has a swelling delayed trigger system, comprising: (i) granules comprising at least one GHB drug(s) and optional biologically active moiety (e.g, one or both in a drug-ion exchange resin complex), at least one gelling agent, at least one swelling enhancer, an optional gas generating agent which generates gas in the presence of stomach acid, optionally, a bulking agent, and (ii) at least one water permeable diffusion barrier coating over the granules of (i), whereby in the presence of stomach acid, a RAFT comprising the swelling delayed trigger system for the drug of (i) is formed. In certain embodiments, a composition of the invention includes granules containing, at a minimum: (i) at least one GHB drug(s) and optional biologically active moiety (drug-ion exchange resin complex, about 20% w/w of trigger, 10% w/w to 50% w/w) (ii) at least one gelling agent HPMCK4M (about 6% w/w, 3% w/w to 15% w/w); (iii) at least one swelling enhancer (about 20%, 10% w/w to 50% w/w) (iv) bulking agent, MCC (about 20% w/w, 10% w/w to 50% w/w). The granules are coated with at least one diffusion barrier PVA (about 15%, 10% w/w to 40% w/w) of the trigger system.

In certain embodiments, the GHB composition has an osmosis delayed trigger system, comprising: (i) granules comprising at least one drug-ion exchange resin complex, at least one gelling agent, at least one osmogent, an optional gas generating agent which generates gas in the presence of stomach acid, an optional bulking agent and (ii) at least one water permeable diffusion barrier coating over the granules of (in), whereby in the presence of stomach acid, a RAFT comprising the osmosis delayed trigger system for the drug of (i) is formed. In certain embodiments, a composition of the invention includes granules containing, at a minimum: (i) at least one GHB and optional biologically active moiety (drug-ion exchange resin complex, about 20% w/w of trigger, 10% w/w to 50% w/w) (ii) at least one gelling agent HPMCK4M (about 8% w/w, 3% w/w to 15% w/w); (iii) at least one osmogent (about 20%, 10% w/w to 50% w/w) (iv) bulking agent, MCC (about 20% w/w, 10% w/w to 50% w/w) in the trigger system. The granules are coated with at least one diffusion barrier PVA (about 15% w/w, 10% w/w to 40% w/w).

In certain embodiments, the composition has two or more different delayed trigger pulse releases.

In certain embodiments, composition comprises two or more different drugs.

In certain embodiments, a Raft comprises two or more different drugs.

In certain embodiments, a Raft comprises the same drug in more than two different release forms.

In certain embodiments, the RAFT formed is initially at least about 15 mm in width as measured in vitro, e.g., using an assay describe in the examples and incorporated by reference herein.

In certain embodiments, the composition comprises two or more different RAFT systems.

In certain embodiments, the raft forming system comprises at least one crosslinkable polysaccharide, at least one crosslinking agent, and at least one gas generating agent which reacts with stomach acid to form a gas. In certain embodiments, the crosslinkable polysaccharide is a galactomannan selected from guar gum, fenugreek gum, or locust bean gum and the at least one cross-linking agent selected from borax, glutaraldehyde, and/or zirconium. In certain embodiments, the RAFT comprises the gelling agent, wherein the gelling agent is liquid at room temperature and gels at body temperature, and is selected from xyloglucan or a poloxamer. In certain embodiments, the RAFT comprises a cubic phase-forming lipid.

Uses

Suitably, the GHB compositions of the invention contain GR Raft forming systems with trigger pulse release, which systems form in vivo in the presence of an acid (e.g., stomach or gastric acid). In certain embodiments, the compositions provide subjects with a timed, pulse release of one or more drug(s), with a first pulse in less than about 3 hours, a second pulse which is a trigger pulse, and optionally, or more additional pulses.

Without wishing to be bound by theory, it is believed that the upon reaction with the acid, a gas generating agent (and/or effervescence couple) in the composition forms a non-toxic gas which enables the GR RAFT containing the GHB drug(s) to remain in the stomach for at least 2 hours, preferably, about 3 hours to 4 hours. It is believed this retention time is caused by the GR Raft exceeding the size of the pyloric valve for at least two hours. Thus, it is believed that the composition forms a GR Raft of at least about 15 mm in width, or more commonly at least about 20 mm in width for this length of time.

The present invention also provides therapeutic methods to treat conditions amenable to treatment by GHB, such as those discussed hereinabove, by administering an effective amount of one or more dosage forms of the invention.

The present dosage forms can be administered to treat a human afflicted with narcolepsy to reduce cataplexy and/or daytime sleepiness.

The present dosage forms can be administered to humans, particularly in the elderly (>50 years old), to improve the quality of sleep, or in conditions in which an increase in growth hormone levels in vivo is desired.

The compositions can also be used to treat fibromyalgia or chronic fatigue syndrome, e.g., to alleviate at least one symptom of fibromyalgia or chronic fatigue syndrome. See, U.S. Pat. No. 5,990,162.

The dosage forms described herein may be provided as a kit comprising, separately packaged, a container comprising an effective amount of the GHB composition in a sachet or other suitable package. For example, the powder may be packaged aluminum foil envelopes, or in a blister pack. The powder can be packaged in many conformations with or without desiccant or other materials to prevent ingress of water. Instruction materials or means, such as printed labeling, can also be included for their administration, e.g., sequentially over a preselected time period and/or at preselected intervals, to yield the desired levels of GHB in vivo for preselected periods of time, to treat a preselected condition.

A kit for treating a patient with a GHB drug, said kit comprising (a) a container comprising a composition according to claim 1; (b) a syringe; (c) a measuring cup; (d) a press-in-bottle adapter; optionally at least one empty pharmacy container with a child-resistant cap.

A daily dose of about the equivalent of about 1 mg/kg to about 50 mg/kg of sodium GHB can be administered to accomplish the therapeutic results disclosed herein. For example, a daily dosage of about 0.5-20 g of the GHB or the equivalent thereto can be administered, preferably about 1 to 15 g, in single or divided doses. In other embodiments, doses may range from about 1.5 g to about 9 g per night, about 4.5 g to about 6 g.

As noted herein above, the compositions may be useful in the treatment of a variety of conditions amenable to treatment by a GHB, such as narcolepsy to reduce cataplexy and/or daytime sleepiness, to improve the quality of sleep, or in conditions in which an increase in growth hormone levels in vivo is desired, and to treat fibromyalgia or chronic fatigue syndrome. The present dosage forms may be used to treat a host of other indications including drug and alcohol abuse, anxiety, cerebrovascular diseases, central nervous system disorders, neurological disorders including Parkinson's Disease and Alzheimer Disease, Multiple Sclerosis, autism, depression, inflammatory disorders, including those of the bowel, such as irritable bowel disorder, regional ileitis and ulcerative colitis, autoimmune inflammatory disorders, certain endocrine disturbances and diabetes.

The compositions may also be administered for the purpose of tissue protection including protection following hypoxia/anoxia such as in stroke, organ transplantation, organ preservation, myocardial infarction or ischemia, reperfusion injury, protection following chemotherapy, radiation, progeria, or an increased level of intracranial pressure, e.g. due to head trauma. The present dosage forms can also be used to treat other pathologies believed to be caused or exacerbated by lipid peroxidation and/or free radicals, such as pathologies associated with oxidative stress, including normal aging. See Patent Publication US 2004/0092455 A 1. The c compositions may also be used to treat movement disorders including restless leg syndrome, myoclonus, dystonia and/or essential tremor. See Frucht et al, *Movement Disorders,* 20(10), 1330 (2005).

As described herein, the GHB compositions of the invention may be dosed orally once per day at bedtime, e.g., between 10 pm-12 pm. This is particularly well suited for treatment of narcolepsy. Optionally, smaller doses may be delivered at bedtime and at different intervals during the night, or in the morning and at intervals during the day. Other variations may be selected depending upon the patient and the indication being treated (e.g., fibromyalgia, etc).

In one embodiment particularly well suited for treatment of narcolepsy, total GHB in the composition is equivalent to about 4.5 to about 9 grams sodium GHB. In certain embodiments, the composition provides a therapeutic effect for about 3.5 to about 8 hours.

A "dissolution rate" refers to the quantity of drug released in vitro from a dosage form per unit time into a release medium. In vitro dissolution rates in the studies described herein were performed on dosage forms placed in a USP Type II or USP type 7 dissolution apparatus set to 37° C.±2° C. under suitable experimental conditions; see, e.g., US2012/007685, incorporated by reference herein. The dissolution media may be purified water, 0.1 N HCl, simulated gastric or intestinal fluid, or other media known in the art.

By "bioavailability" as used herein is intended to estimate area under the curve, or AUC of the active drug in systemic circulation after oral administration as a liquid suspension according to the invention. The AUC is affected by the extent to which the drug is absorbed in the GI tract.

Products are considered to be "bioequivalent" if the relative geometric mean ratio of $C_{max}$, $AUC_{(0-t)}$ and $AUC_{(0-\infty)}$ of the test product to reference product is within the 90% confidence interval of 80% to 125%.

By "sodium oxybate oral solution" is intended the product currently known as Xyrem®, a solution that contains 500 mg sodium oxybate/mL water, adjusted to a pH of 7.5 with malic acid.

The term "$AUC_{0-\infty}$" or "$AUC_{0-inf}$" means the area under the plasma concentration time curve from time 0 to infinity.

The term "$AUC_{0-\infty}$" or "$AUC_{inf}$" is the mean area under the plasma concentration-time curve extrapolated to infinity. It is calculated as the mean of the area under the plasma concentration-time curve from time zero extrapolated to infinity, calculated for each individual participating in the bioavailability study and may be the geometric or arithmetic mean. In general, the drug concentration is measured at certain discrete points in time and the linear trapezoidal rule is used to estimate AUC. Partial AUC may be useful in determining bioequivalence, where the AUC is determined based on a specific fragment of the $AUC_{0-\infty}$. These fragments may be, e.g., from 0-4 hours, 5-8 hours, under fasting and/or fed conditions, or at different intervals, including ½ hour, 1 hour, 4 hours, 6 hours, 7 hours or 8 hours.

"Bioequivalent" means the pharmacokinetic profile of a test composition is within the range of about 80% to about 125% for the 90% confidence interval, when compared to the geometric mean ratio values of one or more of the AUC or the $C_{max}$ of the reference composition.

As used herein, the term "equivalent" to sodium oxybate is used to refer to the weight of the GHB portion of the GHB salt or anion exchange resin complex, without taking into account the weight of the anion exchange resin or any matrix or coating component.

"$C_{max}$" the maximum blood concentration of the GHB active pharmaceutical ingredient after the drug has been orally administered. Unless otherwise specified, the $C_{max}$ values provided herein are geometric mean values.

The term "mean maximum plasma concentration" (mean $C_{max}$) is defined for the purposes of the present invention as the maximum mean blood drug concentration.

"Mean plasma concentration" is the arithmetic mean blood plasma concentration.

Such profiles are especially desirable for diseases such as narcolepsy, cataplexy, movement disorders such as essential tremor and restless leg syndrome, fibromyalgia and chronic fatigue syndrome.

The term "area under the curve (AUC)t" or (0-t) refers to the total drug exposure over time starting at the time the drug is administered and up to 24 hours. In general, the drug concentration is measured at certain discrete points in time and the linear trapezoidal rule is used to estimate AUC.

The words "comprise", "comprises", and "comprising", and "contain", "containing", and "contains" are to be interpreted inclusively rather than exclusively. The words "consist", "consisting", and its variants, are to be interpreted exclusively, rather than inclusively.

As used herein in reference to numeric values provided herein, the term "about" may indicate a variability of as much as 10%.

EXAMPLES

While the invention has been described with reference to exemplary embodiments, it will be understood by those skilled in the art that various changes may be made and equivalents may be substituted for elements thereof without departing from the scope of the invention. Details of the present invention, including its objects and advantages, are provided in the non-limiting exemplary illustrations below.

Example 1. pH as Trigger, Sigmoidal Release System for Generating Second Pulse

TABLE 1

Composition of PR POS

| No. | Ingredients | Gm |
|---|---|---|
|  | GHB - anion exchange resin in first pulse |  |
| 1. | Sodium oxybate | 18 |
| 2. | Cholestyramine | 82 |
|  | PR composition |  |
| 3. | Sodium oxybate | 18 |
| 4. | Microcrystalline cellulose | 26 |
| 5. | Fumaric acid | 8 |
| 6. | Co-povidone | 8 |
| 7. | Eudragit ® EPO | 4 |
| 8. | Calcium carbonate | 6 |
| 9. | Eudragit ® RS | 12 |
| 10. | Triethyl citrate | 2 |
|  | GR carrier composition |  |
| 11. | Iota carrageenan | 20 |
| 12. | Carrageenan kappa | 25 |
| 13. | Calcium carbonate | 20 |
| 14. | Potassium citrate | 10 |
| 15. | Co-Povidone | 4 |
|  | Other excipients |  |
| 16. | HPMC low viscosity | 10 |
| 17. | Sucralose | 8 |
| 18. | Mannitol | 10 |
| 19. | Talc | 10 |
| 20. | Guar Gum | 2.0 |
| 21. | Banana flavor | 6.0 |
| 22. | Sodium benzoate | 1.0 |

I. GHB-Anion Exchange Resin in First Pulse

Weighed quantity of Sodium oxybate was dissolved in 100 ml water. Weight quantity of the resin was added to drug solution under stirring and stirring was continued further for a period of 4 hr. Drug-resin complex was isolated by filtration and dried at 60° C. Drug-resin complex was passed through #60 screen.

II. Preparation of PR Carrier Composition

Weighed quantity of fumaric acid and 8 gm MCC are mixed and granulated using aqueous solution containing 2 gm of copovidone. Wet granules are dried at 60° C. and passed through #40 screen. Granules are coated using Eudragit EPO plasticized using TEC. Coated granules are passed through #40 screen. These granules are mixed with weighed quantities of sodium oxybate and calcium carbonate for 15 min and granulated using 10% w/v solution of copovidone. Wet granules are dried at 60° C. and passed through #40 screen. Granules are coated using Eudragit RS plasticized using triethyl citrate. Coating is performed in Fluid Bed Coater and coated complex is dried at 60° C. Coated granules are passed through #40 screen.

III. Preparation of GR Carrier Composition

Weighed quantities of carrageenan iota, carrageenan kappa, potassium citrate, calcium carbonate are mixed for 15 min and granulated using 10% w/v solution of Co-povidone. Wet granules are dried at 60° C. and passed through #40 screen.

IV. Weighed quantities of GHB-anion exchange resin of step I, coated granules of step II, and granules of step III are mixed with weighed and screened (#40) quantities of HPMC K 100LV, banana flavor, talc, sodium benzoate, mannitol and sucralose for 15 min. For 4.5 gm sodium oxybate dose, 51.25 gm of POS is to be reconstituted using 150 gm purified water at the time of administration.

I. Onset and Duration of Duration of Floating

Amount of suspension equivalent to 4.5 gm sodium oxybate is added to 500 ml SGF without enzyme. The anticipated time required for raft to float and duration of floating are as follows.

| | |
|---|---|
| Onset of floating (minutes) | ≤15 |
| Duration of floating (hours) | 12 |

II. Resiliency of the Raft

Amount of suspension equivalent to 4.5 gm sodium oxybate is added to 500 ml SGF without enzyme. Then it is subjected to agitation using mechanical shaker set at 37° C. and 75 rpm. Anticipated Observation: The raft retains integrity for a period of 12 hours.

III. In Vitro Release Study

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1,2,3,4,6 hours. The anticipated curve is provided in FIG. 2.

Example 2. pH Plus Swelling as Trigger

TABLE 2

Composition of PR POS

| No. | Ingredients | Gm |
|---|---|---|
| | Sodium oxybate in first pulse | |
| 1. | Sodium oxybate | 15 |
| 2. | Microcrystalline cellulose | 15 |
| 3. | Co-povidone | 1 |
| | GHB - anion exchange resin in second pulse | |
| 4. | Sodium oxybate | 15 |
| 5. | Cholestyramine | 85 |
| | PR carrier composition | |
| 6. | Dicalcium phosphate dihydrate | 30 |
| 7. | PVP K30 | 6 |
| 8. | Eudragit ® L100-55 | 30 |
| 9. | Eudragit ® EPO | 35 |
| 10. | Triethyl citrate | 6 |
| | GR carrier composition | |
| 11. | Iota carrageenan | 20 |
| 12. | Pectin | 25 |
| 13. | Gelan gum | 10 |
| 14. | Calcium carbonate | 25 |
| 15. | Sodium bicarbonate | 40 |
| 16. | HPMC K4M | 10 |
| | Other excipients | |
| 17. | HPMC low viscosity | 10 |
| 18. | Sucralose | 8 |
| 19. | Mannitol | 15 |
| 20. | Talc | 14 |
| 21. | Guar Gum | 1.5 |

TABLE 2-continued

Composition of PR POS

| No. | Ingredients | Gm |
|---|---|---|
| 22. | Banana flavor | 8.5 |
| 23. | Sodium benzoate | 1.0 |

I. Sodium Oxybate Granules in First Pulse

Weighed quantity of Sodium oxybate is mixed MCC for 15 min and granulated using 10% w/v solution of co-povidone in water. Wet granules are dried at 60° C. Dried granules are passed through #40 screen.

II. Preparation of Drug Resin Complex

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

III. Preparation of PR Carrier Composition

Weighed quantity of drug resin complex is mixed with weighed quantity of dicalcium phosphate dehydrate and granulated using PVP solution. Granules are dried and passed through #60 screen. Granules are coated with Eudragit L100-55 plasticized using triethyl citrate. Coated granules are further coated with Eudragit EPO plasticized by TEC. Coated granules are passed through #40 screen.

IV. Preparation of GR Carrier Composition

Weighed quantities of carrageenan iota, pectin, gelan gum, calcium carbonate, sodium bicarbonate, HPMC K4M are mixed for 15 min and granulated. Wet granules are dried at 60° C. and passed through #40 screen.

V. The granules of step I, coated granules of step III, and granules of step IV are mixed with weighed and screened (#40) quantities of HPMC K100LV, banana flavor, talc, sodium benzoate, mannitol and sucralose for 15 min. For 4.5 gm sodium oxybate dose, 63.9 gm of POS is to be reconstituted using 190 gm purified water at the time of administration.

In-Vitro Testing

I. Onset and Duration of Duration of Floating

Amount of reconstituted suspension equivalent to 4.5 gm of sodium oxybate is added to 500 ml SGF without enzyme. The anticipated time required for raft to float and duration of floating are as follows.

| | |
|---|---|
| Onset of floating (minutes) | ≤25 |
| Duration of floating (hours) | 12 |

II. Resiliency of the Raft

Amount of reconstituted suspension equivalent to 4.5 gm of sodium oxybate is added to 500 ml SGF without enzyme 0.1N HCl solution. Then it is subjected to agitation using mechanical shaker set at 37° C. and 75 rpm. Anticipated Observation: The retains integrity for a period of 12 hours.

In Vitro Release Study

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1,2,3,4,6, 8 hours. The anticipated curve is provided in FIG. 3.

Example 3. Swelling as Trigger to Generate Second Pulse

TABLE 3

Composition of PR POS

| No. | Ingredients | Gm |
|---|---|---|
| | GHB - anion exchange resin first pulse | |
| 1. | Sodium oxybate | 18 |
| 2. | Cholestyramine | 82 |
| | GHB - anion exchange resin in second pulse | |
| 3. | Sodium oxybate | 18 |
| 4. | Cholestyramine | 82 |
| | PR carrier composition | |
| 5. | MCC | 7 |
| 6. | HPMC K4M | 3.5 |
| 7. | Cross-povidone | 10.5 |
| 8. | Calcium carbonate | 7 |
| 9. | Kollicoat ® SR 30D | 14 |
| 10. | Triacetin | 1 |
| 11. | PVP K30 | 3 |
| | GR carrier composition | |
| 12. | Iota carrageenan | 25 |
| 13. | Pectin | 30 |
| 14. | Calcium carbonate | 25 |
| 15. | Gelan gum | 10 |
| 16. | Co-Povidone | 5 |
| | Other excipients | |
| 17. | HPMC low viscosity | 10 |
| 18. | Sucralose | 8 |
| 19. | Mannitol | 12 |
| 20. | Talc | 10 |
| 21. | Guar Gum | 2.0 |
| 22. | Banana flavor | 8.0 |

I. Preparation of Drug Resin Complex

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of drug resin complex for second pulse is mixed with weighed quantities of MCC, HPMC K4M, Crospovidone, calcium carbonate for 15 min and granulated using 10% w/v solution of PVP K30. Wet granules are dried at 60° C. and passed through #40 screen. Triacectin is added in purified water under stirring and continue stirring to get clear solution. Triacetin solution is added gradually to Kollicoat® SR30D dispersion under stirring and continue stirring for 1 hr. The coating dispersion is screened through sieve #40. The dried granules are coated using the prepared dispersion and stirring is continued throughout the coating process. Coating is performed in Fluid Bed Coater and coated complex is dried at 60° C. Coated complex is passed through #40 screen.

III. Preparation of GR Carrier Composition

Weighed quantity of drug resin complex for first pulse is mixed with weighed quantities of carrageenan iota, pectin, gelan gum, calcium carbonate for 15 min and granulated using 10% w/v solution of Co-povidone. Wet granules are dried at 60° C. and passed through #40 screen.

IV. The granules of step II, granules of step III are mixed for 15 min with weighed and screened (#40) quantities of HPMC K100LV, banana flavor, talc, mannitol and sucralose. For 4.5 gm sodium oxybate dose, 48.8 gm of POS is to be reconstituted using 150 gm purified water at the time of administration.

Onset and Duration of Duration of Floating

Amount of suspension equivalent to 4.5 gm sodium oxybate is added to 500 ml SGF without enzyme. The anticipated time required for raft to float and duration of floating areas follows.

| | |
|---|---|
| Onset of floating (minutes) | ≤20 |
| Duration of floating (hours) | 12 |

III. Resiliency of the Raft

Amount of suspension equivalent to 4.5 gm sodium oxybate is added to 500 ml SGF without enzyme 0.1N HCl solution. Then it is subjected to agitation using mechanical shaker set at 37° C. and 75 rpm. Anticipated Observation: The raft retains integrity for a period of 12 hours.

III. In Vitro Release Study

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1,2,3,4,6 hours. The anticipated curve is provided in FIG. 4.

Example 4. Swelling as Trigger to Generate Second Pulse

TABLE 4

Composition of PR POS

| No. | Ingredients | Gm |
|---|---|---|
| | Sodium oxybate granules in first pulse | |
| 1. | Sodium oxybate | 18 |
| 2. | Microcrystalline cellulose | 18 |
| 3. | Co-povidone | 1 |
| | GHB - anion exchange resin in second pulse | |
| 4. | Sodium oxybate | 18 |
| 5. | Cholestyramine | 82 |
| | PR carrier composition | |
| 6. | MCC | 7 |
| 7. | HPMC K4M | 7 |
| 8. | Cross-povidone | 7 |
| 9. | Calcium carbonate | 7 |
| 10. | Kollicoat ® SR 30D | 14 |
| 11. | Triacetin | 1 |
| 12. | PVP K30 | 3 |
| | GR carrier composition | |
| 13. | Iota carrageenan | 20 |
| 14. | Pectin | 25 |
| 15. | Calcium carbonate | 20 |
| 16. | Gelan gum | 10 |
| 17. | Co-Povidone | 4 |
| | Other excipients | |
| 18. | HPMC low viscosity | 10 |
| 19. | Sucralose | 8 |
| 20. | Mannitol | 10 |

TABLE 4-continued

| Composition of PR POS | | |
|---|---|---|
| No. | Ingredients | Gm |
| 21. | Talc | 10 |
| 22. | Guar Gum | 2.0 |
| 23. | Banana flavor | 6.0 |
| 24. | Sodium benzoate | 1.0 |

I. Sodium Oxybate Granules in First Pulse

Weighed quantity of Sodium oxybate is mixed MCC for 15 min and granulated using 10% w/v solution of co-povidone in water. Wet granules are dried at 60° C. Dried granules are passed through #40 screen.

II. Preparation of Drug-Anion Resin Complex

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

III. Preparation of PR Carrier Composition

Weighed quantity of drug resin complex is mixed with weighed quantities of MCC, HPMC K4M, Crospovidone, calcium carbonate for 15 min and granulated using 10% w/v solution of PVP K30. Wet granules are dried at 60° C. and passed through #40 screen. Triacetin is added in purified water under stirring and continue stirring to get clear solution. Triacetin solution is added gradually to Kollicoat® SR30D dispersion under stirring and continue stirring for 1 hr. The coating dispersion is screened through sieve #40. The dried granules are coated using the prepared dispersion and stirring is continued throughout the coating process. Coating is performed in Fluid Bed Coater and coated complex is dried at 60° C. Coated complex is passed through #40 screen.

IV. Preparation of GR Carrier Composition

Weighed quantities of carrageenan iota, pectin, gelan gum, calcium carbonate are mixed for 15 min and granulated using 10% w/v solution of Co-povidone. Wet granules are dried at 60° C. and passed through #40 screen.

V. The granules of step I, coated granules of step III, and granules of step IV are mixed with weighed and screened (#40) quantities of HPMC K100LV, banana flavor, talc, sodium benzoate, mannitol and sucralose for 15 min. For 4.5 gm sodium oxybate dose, 38.625 gm of POS is to be reconstituted using 115 gm purified water at the time of administration.

I. Onset and Duration of Duration of Floating

Amount of suspension equivalent to 4.5 gm sodium oxybate is added to 500 ml SGF without enzyme. The anticipated time required for raft to float and duration of floating are as follows.

| Onset of floating (minutes) | ≤15 |
|---|---|
| Duration of floating (hours) | 12 |

II. Resiliency of the Raft

Amount of suspension equivalent to 4.5 gm sodium oxybate is added to 500 ml SGF without enzyme 0.1N HCl solution. Then it is subjected to agitation using mechanical shaker set at 37° C. and 75 rpm. Anticipated Observation: The raft is found to retain integrity for a period of 12 hours.

III. In Vitro Release Study

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1,2,3,4,6 hours. The anticipated curve is provided in FIG. 5.

Example 5. Osmosis Plus Swelling as Trigger to Generate Second Pulse

TABLE 5

| Composition of PR POS | | |
|---|---|---|
| No. | Ingredients | Gm |
| | Sodium oxybate granules in first pulse | |
| 1. | Sodium oxybate | 18 |
| 2. | Microcrystalline cellulose | 18 |
| 3. | Co-povidone | 1 |
| | GHB - anion exchange resin in second pulse | |
| 4. | Sodium oxybate | 18 |
| 5. | Cholestyramine | 82 |
| | PR carrier composition | |
| 6. | MCC | 7 |
| 7. | HPMC K4M | 7 |
| 8. | Mannitol | 15 |
| 9. | Calcium carbonate | 6 |
| 10. | Kollicoat ® SR 30D | 14 |
| 11. | Triacetin | 1 |
| 12. | PVP K30 | 3 |
| | GR carrier composition | |
| 13. | Iota carrageenan | 20 |
| 14. | Carrageenan kappa | 25 |
| 15. | Calcium carbonate | 20 |
| 16. | Potassium citrate | 10 |
| 17. | Co-Povidone | 4 |
| | Other excipients | |
| 18. | HPMC low viscosity | 10 |
| 19. | Sucralose | 8 |
| 20. | Mannitol | 10 |
| 21. | Talc | 10 |
| 22. | Guar Gum | 2.0 |
| 23. | Banana flavor | 6.0 |
| 24. | Sodium benzoate | 1.0 |

I. Sodium Oxybate Granules in First Pulse

Weighed quantity of Sodium oxybate is mixed MCC for 15 min and granulated using 10% w/v solution of co-povidone in water. Wet granules are dried at 60° C. Dried granules are passed through #40 screen.

II. Preparation of Drug Resin Complex

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

III. Preparation of PR Carrier Composition

Weighed quantity of drug resin complex is mixed with weighed quantities of MCC, HPMC K4M, Mannitol, calcium carbonate for 15 min and granulated using 10% w/v solution of PVP K30. Wet granules are dried at 60° C. and passed through #40 screen. Triacetin is added in purified water under stirring and continue stirring to get clear solution. Triacetin solution is added gradually to Kollicoat® SR30D dispersion under stirring and continue stirring for 1 hr. The coating dispersion is screened through sieve #40. The dried granules are coated using the prepared dispersion and stirring is continued throughout the coating process. Coating is performed in Fluid Bed Coater and coated complex is dried at 60° C. Coated complex is passed through #40 screen.

IV. Preparation of GR Carrier Composition

Weighed quantities of carrageenan iota, carrageenan kappa, potassium citrate, calcium carbonate are mixed for 15 min and granulated using 10% w/v solution of Co-povidone. Wet granules are dried at 60° C. and passed through #40 screen.

V. The granules of step I, coated granules of step III, and granules of step IV are mixed with weighed and screened (#40) quantities of HPMC K100LV, banana flavor, talc, sodium benzoate, mannitol and sucralose for 15 min. For 4.5 gm sodium oxybate dose, 39.375 gm of POS is to be reconstituted using 118 gm purified water at the time of administration.

Onset and Duration of Duration of Floating

Amount of suspension equivalent to 4.5 gm sodium oxybate is added to 500 ml SGF without enzyme. Onset of floating is anticipated in under 20 minutes and duration of floating is anticipated to be 12 hours.

I. Resiliency of the Raft

Amount of suspension equivalent to 4.5 gm sodium oxybate is added to 500 ml SGF without enzyme 0.1N HCl solution. Then it is subjected to agitation using mechanical shaker set at 37° C. and 75 rpm. Anticipated Observation: The raft retains integrity for a period of 12 hours.

II. In Vitro Release Study

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1,2,3,4,6,8 hours.

Example 6. Erosion as Trigger

TABLE 6

Composition of PR POS

| No. | Ingredients | Gm |
|---|---|---|
| | GHB - anion exchange resin first pulse | |
| 1. | Sodium oxybate | 15 |
| 2. | Cholestyramine | 85 |
| | GHB - anion exchange resin in second pulse | |
| 3. | Sodium oxybate | 15 |
| 4. | Cholestyramine | 85 |
| | PR carrier composition | |
| 5. | MCC | 30 |
| 6. | PVP K30 | 3 |
| 7. | Calcium carbonate | 10 |
| 8. | HPMC K4M | 7 |
| 9. | PEG400 | 0.7 |
| | GR carrier composition | |
| 10. | Iota carrageenan | 20 |
| 11. | Pectin | 15 |
| 12. | Gelan gum | 15 |

TABLE 6-continued

Composition of PR POS

| No. | Ingredients | Gm |
|---|---|---|
| 13. | Calcium carbonate | 20 |
| 14. | HPMC K4M | 15 |
| | Other excipients | |
| 15. | HPMC K100LV | 10.6 |
| 16. | Sucralose | 8.5 |
| 17. | Mannitol | 17 |
| 18. | Talc | 14 |
| 19. | Guar Gum | 1.7 |
| 20. | Banana flavor | 8.5 |
| 21. | Sodium benzoate | 1.0 |

I. Preparation of Drug Resin Complex

Weighed quantity of sodium oxybate is dissolved in 500 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of PR Carrier Composition

Weighed quantity of drug resin complex for second pulse is mixed with weighed quantities of MCC, HPMCK4M, calcium carbonate for 15 min and granulated using 10% w/v solution of PVP K30. Wet granules are dried at 60° C. and passed through #40 screen. Dried granules are coated in fluidized bed processor using HPMC K100LV plasticized using PEG 400. Coated granules are dried at 60° C. Coated granules are passed through #30 screen.

III. Preparation of GR Carrier Composition

Weighed quantities of carrageenan iota, pectin, gelan gum, calcium carbonate, and HPMC K4M are mixed for 15 min and granulated. Wet granules are dried at 60° C. and passed through #40 screen.

IV. Weighed quantity of drug resin complex for first pulse, the granules of step II, and granules of step III are mixed with weighed and screened (#40) quantities of HPMC K100LV, banana flavor, talc, sodium benzoate, mannitol and sucralose for 15 min. For 4.5 gm sodium oxybate equivalent dose, 59.4 gm of POS is to be reconstituted using 240 gm purified water at the time of administration.

In-Vitro Testing

I. Onset and Duration of Duration of Floating

Amount of reconstituted suspension equivalent to 4.5 gm of sodium oxybate is added to 500 ml SGF without enzyme. The anticipated time required for raft to float and duration of floating are noted.

| Onset of floating (minutes) | ≤20 |
|---|---|
| Duration of floating (hours) | 12 |

II. Resiliency of the Raft

Amount of reconstituted suspension equivalent to 4.5 gm of sodium oxybate is added to 500 ml SGF without enzyme 0.1N HCl solution. Then it is subjected to agitation using mechanical shaker set at 37° C. and 75 rpm. The anticipated observation: The raft retains integrity for a period of 12 hours.

All patents, patent publications, and other publications listed in this specification, are incorporated herein by reference. U.S. Patent Application No. 62/607,159, filed Dec. 18, 2017, is incorporated by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. An orally administrable drug powder composition which forms a gastro-retentive RAFT having at least two trigger pulses, the composition comprising:
   (a) at least one drug in a first pulse which releases in less than about 3 hours;
   (b) at least one drug in a delayed trigger release form;
   (c) at least one non-toxic gas generating agent; and
   (d) a RAFT system, and
      wherein following oral ingestion, the composition provides a self-assembling gastro-retentive RAFT having entrapped therein, the at least one drug of (a) and (b) and the gas generated in situ by the non-toxic gas generating agent, thereby providing a floating gastro-retentive RAFT having a dual pulse system wherein at least the second pulse is a trigger pulse and which retains the at least one drug in the stomach for at least about 3 hours,
   wherein the at least one drug of (a) and (b) is an active pharmaceutical ingredient (API) which is a free base or acid, or a pharmaceutically acceptable salt, solvate or hydrate, thereof,
   wherein the at least one drug comprises a gamma hydroxybutyrate or its salts, hydrates, tautomers, or solvates, or mixtures thereof,
   wherein the at least one delayed trigger release form of (b) comprises a pH sigmoidal delayed trigger system, an erosion delayed trigger system, a pH plus swelling delayed trigger system or a swelling delayed trigger system.

2. The orally administrable powder composition according to claim 1, wherein the RAFT has two or more different delayed trigger pulse releases.

3. The orally administrable powder composition according to claim 1, wherein the RAFT formed is initially at least 2 cm in size.

4. The orally administrable powder composition according to claim 1, wherein the composition comprises two or more different RAFT systems.

5. The orally administrable powder composition according to claim 1, wherein the raft forming system comprises at least one crosslinkable polysaccharide, at least one cross-linking agent, and at least one gas generating agent which reacts with stomach acid to form a gas.

6. The orally administrable drug composition according to claim 5, wherein the crosslinkable polysaccharide is a galactomannan selected from guar gum, fenugreek gum, or locust bean gum and the at least one cross-linking agent selected from borax, glutaraldehyde, and/or zirconium.

7. The orally administrable drug composition according to claim 1, wherein the RAFT comprises a gelling agent which comprises the crosslinkable polymer and crosslinking agent, wherein the gelling agent is liquid at room temperature and gels at body temperature, and is selected from xyloglucan or a poloxamer.

8. An orally administrable drug powder composition which forms a gastro-retentive RAFT having at least two trigger pulses, the composition comprising:
   (a) at least one drug in a first pulse which releases in less than about 3 hours;
   (b) at least one drug in a delayed trigger release form;
   (c) at least one non-toxic gas generating agent; and
   (d) a RAFT system, and
      wherein following oral ingestion, the composition provides a self-assembling gastro-retentive RAFT having entrapped therein, the at least one drug of (a) and (b) and the gas generated in situ by the non-toxic gas generating agent, thereby providing a floating gastro-retentive RAFT having a dual pulse system wherein at least the second pulse is a trigger pulse and which retains the at least one drug in the stomach for at least about 3 hours,
   wherein the RAFT is a liquid crystal RAFT comprising a cubic phase-forming lipid
   wherein the at least one drug of (a) and (b) is an active pharmaceutical ingredient (API) which is a free base or acid, or a pharmaceutically acceptable salt, solvate or hydrate, thereof,
   wherein the at least one drug comprises a gamma hydroxybutyrate or its salts, hydrates, tautomers, or solvates, or mixtures thereof,
   wherein the at least one delayed trigger release form of (b) comprises a pH sigmoidal delayed trigger system, an erosion delayed trigger system, a pH plus swelling delayed trigger system or a swelling delayed trigger system.

9. The orally administrable drug composition according to claim 8, wherein the gas-generating agent is selected from carbonates or bicarbonates of an alkali or alkaline earth metal, sulfites, or combinations thereof, or combinations thereof with an acid source which create a gas-generating couple.

10. The orally administrable drug composition according to claim 9, wherein the carbonate or bicarbonate of an alkali or alkaline earth metal are selected from potassium carbonate, potassium bicarbonate, sodium carbonate, sodium bicarbonate, calcium carbonate, sodium glycine carbonate, magnesium carbonate, or aluminum carbonate.

11. The orally administrable powder composition according to claim 8, wherein the at least one drug, selected from a gamma hydroxybutyrate or its salts, hydrates, tautomers, or solvates, or mixtures thereof, is at least sodium oxybate, calcium oxybate, magnesium oxybate, potassium oxybate, or lithium oxybate.

12. The orally administrable powder composition according to claim 1, wherein the RAFT formed is initially at least 15 mm in width.

* * * * *